(12) United States Patent
Shipp et al.

(10) Patent No.: US 7,632,660 B2
(45) Date of Patent: *Dec. 15, 2009

(54) LYMPHOMA ASSOCIATED MOLECULES AND USES THEREFOR

(75) Inventors: Margaret A. Shipp, Wellesley, MA (US); Ricardo Aguiar, Chestnut Hill, MA (US); Liqun Gu, Plainsboro, MA (US); Kunihiko Takeyama, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 524 days.

This patent is subject to a terminal disclaimer.

(21) Appl. No.: 11/125,015

(22) Filed: May 9, 2005

(65) Prior Publication Data

US 2007/0259342 A1 Nov. 8, 2007

Related U.S. Application Data

(63) Continuation of application No. 09/957,635, filed on Sep. 19, 2001, now Pat. No. 7,112,420.

(60) Provisional application No. 60/233,791, filed on Sep. 19, 2000.

(51) Int. Cl.
*C12P 21/00* (2006.01)
*C07K 14/00* (2006.01)
*C07H 21/04* (2006.01)

(52) U.S. Cl. .......................... 435/69.1; 530/350; 514/2

(58) Field of Classification Search ........................ None
See application file for complete search history.

(56) References Cited

FOREIGN PATENT DOCUMENTS

| WO | WO 00/12698 | 3/2000 |
|---|---|---|
| WO | WO 00/26231 | 5/2000 |
| WO | WO 01/53453 | 7/2001 |

OTHER PUBLICATIONS

Paul (fundamental Immunology (text) 1993, pp. 247-251.*
EMBL Acc. No. AC026506 for *Homo sapiens* chromosome 3 clone RP11-757112 map 3, Working Draft Sequence, 33 unordered pieces.
Aguiar et al. "TEL-AML1 fusion in acute lymphoblastic leukaemia of adults." *Br. J. Haematol.* Dec. 1996;95(4):673-677.
Aguiar et al. "PTPROt: an alternatively spliced and developmentally regulated B-lymphoid phosphatase that promotes G0/G1 arrest." *Blood* Oct. 1, 1999;94(7):2403-2413.
Alizadeh et al. "Distinct types of diffuse large B-cell lymphoma identified by gene expression profiling." *Nature* 2000;403:503-511.
Bleul et al. "A highly efficacious lymphocyte chemoattractant, stromal cell-derived factor 1 (SDF-1)." *J. Exp. Med.* Sep. 1, 1996;184(3):1101-1109.
Bretscher "Regulation of cortical structure by the ezrin-radixin-moesin protein family." *Curr. Opin. Cell Biol.* Feb. 1999;11(1):109-116.

Burger et al. "Chronic lymphocytic leukemia B cells express functional CXCR4 chemokine receptors that mediate spontaneous migration beneath bone marrow stromal cells." *Blood* Dec. 1, 1999;94(11):3658-3667.
Cabanillas et al. "Frequent nonrandom chromosome abnormalities in 27 patients with untreated large cell lymphoma and immunoblastic lymphoma." *Cancer Res.* Oct. 1, 1988;48(19):5557-5564.
Cigudosa et al. "Cytogenetic analysis of 363 consecutively ascertained diffuse large B-cell lymphomas." *Genes, Chromosomes & Cancer* 1999;25:123-133.
Costanzi et al. "Histone macroH2A1 is concentrated in the inactive X chromosome of female mammals." *Nature* Jun. 11, 1998;393(6685):599-601.
Duan et al. "Characterization of the VHL tumor suppressor gene product: localization, complex formation, and the effect of natural inactivating mutations." *PNAS USA* Jul. 3, 1995;92(14):6459-6463.
Förster et al. "CCR7 coordinates the primary immune response by establishing functional microenvironments in secondary lymphoid organs." *Cell* Oct. 1, 1999;99(1):23-33.
Freemont et al. "A novel cysteine-rich sequence motif." *Cell* Feb. 8, 1991;64(3):483-484.
Horwitz et al. "Cell migration-movin' on." *Science* 1999;286(5442)1102-3.
Khokhar et al. "Cytogenetic abnormalities in the leukemic phase of non-Hodgkin lymphoma." *Cancer Genet. Cytogenet.* Aug. 1995;83(1):18-24.
Lankes et al. "Moesin: a member of the protein 4.1-talin-ezrin family of proteins" *PNAS USA* Oct. 1, 1991;88(19):8297-301.
de Leval et al. "Nodal diffuse large B-cell lymphomas (DLB-CLs) are more likely to be derived from germinal center B-cells than extranodal DLB-CLs." *Blood* 1999;94:521a.
Liang et al. "Differential display of eukaryotic messenger RNA by means of the polymerase chain reaction." *Science* Aug. 14, 1992;257(5072):967-71.
Lupas "Predicting coiled-coil regions in proteins." *Curr. Opin. Struct. Biol.* Jun. 1997;7(3):388-63.
Maloisel et al. "Emergence of unusual cytogenetic abnormalities under interferon-alpha therapy in patients with chronic myelogenous leukemia." *Cancer Genet. Cytogenet.* Sep. 1999;113(2):172-6.
Matsuno et al. "Human deltex is a conserved regulator of Notch signalling." *Nat. Genet.* May 1998;19(1):74-8.
Mitelman et al. "A breakpoint map of recurrent chromosomal rearrangements in human neoplasia." *Nat. Genet.* 1997;15 Spec No. 417-474.

(Continued)

*Primary Examiner*—Karen A Canella
(74) *Attorney, Agent, or Firm*—Foley Hoag, LLP

(57) ABSTRACT

The invention provides isolated nucleic acids molecules, designated BBAP nucleic acid molecules, which encode proteins that interact with or bind to BAL molecules, which are differentially expressed in non-Hodgkin's lymphoma. The invention also provides antisense nucleic acid molecules, recombinant expression vectors containing BBAP nucleic acid molecules, host cells into which the expression vectors have been introduced, and non-human transgenic animals in which a BBAP gene has been introduced or disrupted. The invention still further provides isolated BBAP proteins, fusion proteins, antigenic peptides and anti-BBAP antibodies. Diagnostic methods using compositions of the invention are also provided.

5 Claims, 5 Drawing Sheets

OTHER PUBLICATIONS

Monni et al. "Gain of 3q and deletion of 11q22 are frequent aberrations in mantle cell lymphoma." *Genes, Chromosomes, Cancer*. Apr. 1998;21(4):298-307.

Nagase et al. "Prediction of the coding sequences of unidentified human genes. XV. The complete sequences of 100 new cDNA clones from brain which code for large proteins in vitro." *DNA Res*. Oct. 29, 1999;6(5):337-345.

Ohno "Gene duplication and the uniqueness of vertebrate genomes circa 1970-1999." *Semin. Cell Dev. Biol*. Oct. 1999;10(5):517-522.

Pampeno et al. "A novel cDNA transcript expressed in fractionated X-irradiation-induced murine thymomas." *Cell Growth & Differentation* 1996;7:1113-1123.

Pehrson et al. "MacroH2A, a core histone containing a large nonhistone region." *Science*. Sep. 4, 1992;257(5075)1398-400.

Pehrson et al. "Evolutionary conservation of histone macroH2A subtypes and domains." *Nucleic Acids Res*. Jun. 15, 1998;26(12):2837-2842.

Ren et al. "Identification of a ten-amino acid proline-rich SH3 binding site." *Science*. Feb. 19, 1993;259(5098):1157-1161.

Salgia et al. "Expression of the focal adhesion protein paxillin in lung cancer and its relation to cell motility." *Oncogene* Jan. 7, 1999;18(1):67-77.

Schlegelberger et al. "Clinicopathogenetic significance of chromosomal abnormalities in patients with blastic peripheral B-cell lymphoma. Kiel-Wien-Lymphoma Study Group." *Blood* Nov 1, 1999;94(9):3114-3120.

Schouten et al. "Chromosomal abnormalities in untreated patients with non-Hodgkin's lymphoma: associations with histology, clinical characteristics, and treatment outcome." *Blood* May 1, 1990;75(9):1841-1847.

Shipp et al. "A predictive model for aggressive non-Hodgkin's lymphoma." *N. Engl. J. Med*. Sep. 30, 1993;329(14):987-994.

Shipp "Prognostic factors in aggressive non-Hodgkin's lymphoma: who has (high-risk) disease?" *Blood* Mar. 1, 1994;83(5):1165-1173.

Shipp "Can we improve upon the International Index?" *Ann. Oncol*. 1997;8 Suppl 1:43-47.

Shipp et al. "Non-Hodgkin's lymphomas." In DeVita VT, Hellman et al. eds. *Cancer Principles & Practices of Oncology*, Philadelphia, PA, JB Lippincott Company 1997;2165-2220.

Shipp et al. "International Consensus Conference on High-Dose Therapy with Hematopoietic Stem Cell Transplantation in Aggressive Non-Hodgkin's Lymphomas: report of the jury." *J. Clin. Oncol*. Jan. 1999;17(1):423-429.

Smith et al. "Tankyrase, a poly(ADP-ribose) polymerase at human telomeres." *Science* Nov. 20, 1998;282(5393):1484-1487.

Smith et al. Vertebrate genome evolution: a slow shuffle or a big bang? *Bioassays* 1999;8:697-703.

Testoni et al. "3q21 and 3q26 cytogenetic abnormalities in acute myeloblastic leukemia: biological and clinical features." *Haematologica* Aug. 1999;84(8):690-694.

Trentin et al. "The chemokine receptor CXCR3 is expressed on malignant B cells and mediates chemotaxis." *J. Clin. Invest*. Jul. 1999;104(1):115-21.

Weiss et al. "The mammalian myosin heavy chain gene family." *Annu. Rev. Cell Dev. Biol*. 1996;12:417-439.

Xiao et al. "FGFR1 is fused with a novel zinc-finger gene, ZNF198, in the t(8;13) leukaemia/lymphoma syndrome." *Nat. Genet*. Jan. 1998;18(1):84-7.

Accession No. A1274035, NCI-CGAP, Jan. 29, 1999.

New England Biolabs Catalg, 1993-1994, p. 91.

Eck et al., Gene-Based Therapy, In: The Pharmacological Basis of Therapeutics, Goodman and Gilman, Ed s., pp. 77-101 (1996).

Orkin et al., "Report and Recommendation of the Panel to Assess the NIH Investment in Research on Gene Therapy," NIH (1995).

Verma et al., "Gene therapy—promises, problems and prospects," *Nature*, 389A:239-242 (1997).

* cited by examiner

BBAP cDNA

```
CCCTCGACCTCGAGATCCATTGTGCTCTAAAGGCGGCTCTGCCGGGAACA
GGGAGGGACCTCCAGGGAAGCGAAACTGAAACTTTGCGCCCAGTCCGCA
GGGCGGGCCGCGCCTTTACCGCCCAGCTGCCTCCCGGAGCCCCCGCGCCC
TCCCGACGCGCAGAGCCATGGCCTCCCACCTGCGCCCGCCGTCCCCGCTCC
TCGTGCGGGTGTACAAGTCCGGCCCCGAGTACGAAGGAAGCTGGAGAGC
TACTTCCAGAGCTCTAAGTCCTCGGGCGGCGGGGAGTGCACGGTCAGCAC
CCAGGAACACGAAGCCCCGGGCACCTTCCGGGTGGAGTTCAGTGAAAGG
GCAGCTAAGGAGAGAGTGTTGAAAAAGGAGAGCACCAAATACTTGTTG
ACGAAAAACCTGTGCCCATTTTCCTGGTACCCACTGAAAATTCAATAAAG
AAGAACACGAGACCTCAAATTTCTTCACTGACACAATCACAAGCAGAAAC
ACCGTCTGGTGATATGCATCAACATGAAGGACATATTCCTAATGCTGTGG
ATTCCTGTCTCCAAAAGATCTTTCTTACTGTAACAGCTGACCTGAACTGTA
ACCTGTTCTCCAAAGAGCAGAGGGCATACATAACCACACTGTGCCCTAGT
ATCAGAAAAATGGAAGGTCACGATGGAATTGAGAAGGTGTGTGGTGACTT
CCAAGACATTGAAAGAATACATCAATTTTTGAGTGAGCAGTTCCTGGAAA
GTGAGCAGAAACAACAATTTTCCCCTTCAATGACAGAGAGGAAGCCACTC
AGTCAGCAGGAGAGGGACAGCTGCATTTCTCCTTCTGAACCAGAAACCAA
GGCAGAACAAAAAAGCAACTATTTTGAAGTTCCCTTGCCTTACTTTGAATA
CTTTAAATATATCTGTCCTGATAAAATCAACTCAATAGAGAAAGATTTG
GTGTAAACATTGAAATCCAGGAGAGTTCTCCAAATATGGTCTGTTTAGATT
TCATCTCAAGTCGATCAGGTGACCTGGAAGCAGCTCGTGAGTCTTTTGCTA
GTGAATTTCAGAAGAACACAGAACCTCTGAAGCAAGAATGTGTCTCTTTA
GCAGACAGTAAGCAGGCAAATAAATTCAAACAGGAATTGAATCACCAGTT
TACAAAGCTCCTTATAAAGGAGAAAGGAGGCGAATTAACTCTCCTTGGGA
CCCAAGATGACATTTCAGCTGCCAAACAAAAAATCTCTGAAGCTTTTGTC
AAGATACCTGTGAAACTATTTGCTGCCAATTACATGATGAATGTAATTGA
GGTTGATAGTGCCCACTATAAACTTTTAGAAACTGAATTACTACAGGAGA
TATCAGAGATCGAAAAAAGGTATGACATTTGCAGCAAGGTTTCTGAGAAA
GGTCAGAAAACCTGCATTCTGTTTGAATCCAAGGACAGGCAGGTAGATCT
ATCTGTGCATGCTTATGCAAGTTTCATCGATGCCTTTCAACATGCCTCATG
TCAGTTGATGAGAGAAGTTCTTTTACTGAAGTCTTTGGGCAAGGAGAGAA
AGCACTTACATCAGACCAAGTTTGCTGATGACTTTAGAAAAAGACATCCA
AATGTACACTTTGTGCTAAATCAAGAGTCAATGACTTTGACTGGTTTGCCA
AATCACCTTGCAAAGGCGAAGCAGTATGTTCTAAAAGGAGGAGGAATGTC
TTCATTGGCTGGAAAGAAATTGAAAGAGGGTCATGAAACACCGATGGACA
TTGATAGCGATGATTCCAAAGCAGCTTCTCCGCCACTCAAGGGCTCTGTGA
GTTCTGAGGCCTCAGAACTGGACAAGAAGGAAAAGGGCATCTGTGTCATC
TGTATGGACACCATTAGTAACAAAAAAGTGCTACCAAAGTGCAAGCATGA
ATTCTGCGCCCCTTGTATCAACAAAGCCATGTCATATAAGCCAATCTGTCC
CACATGCCAGACTTCCTATGGTATTCAGAAAGGAAATCAGCCAGAGGGAA
GCATGGTTTTCACTGTTTCAAGAGACTCACTTCCAGGTTATGAGTCCTTTG
GCACCATTGTGATTACTTATTCTATGAAAGCAGGCATACAAACAGAAGAA
CACCCAAACCCAGGAAAGAGATACCCTGGAATACAGCGAACTGCATACTT
GCCTGATAATAAGGAAGGAAGGAAGGTTTTGAAACTGCTTTATAGGGCCT
TTGACCAAAAGCTGATTTTTACAGTGGGGTACTCTCGCGTATTAGGAGTCT
CAGATGTCATCACTTGGAATGATATTCACCACAAAACATCCCGGTTTGGA
GGACCAGAAATGTATGGCTATCCTGATCCTTCTTACCTGAAACGTGTCAAA
GAGGAGCTGAAAGCCAAAGGAATTGAGTAAGACAACTGCTGGAAGATGT
```

FIGURE 1

CTTAAATCAAGCTTTCAAAAAAATATATTTTAGGAGGCTGATTTAATGCCA
GTCTAAATCCTTATGTAGAAAGGACTTTGAAATTTTTCTTCTCAAGAAATG
GTTTGTATAAGAATAACAATCTGCTAGTCTGTCATTTCTGGAGTGATACTT
TTTTTTTTGAGACGGAGTCTGCTCTGTCGCTCGCACTGGAGTGCAGTGGCA
TGATCTCGGCTCACTGCAAGCTCCGCCTCCCAGGTTCATGCCATTCTCCTA
CCTCAGCCTCCCGAGTAGCTGGGACTACAGGCGCCCACTTTAGAGCACAA
TGGATCTCGAGGAACATTCTCTCTTCAAAAAGAAAAAGGTGAAGACCT

BBAP protein

MASHLRPPSPLLVRVYKSGPRVRRKLESYFQSSKSSGGGECTVSTQEHEAPGT
FRVEFSERAAKERVLKKGEHQILVDEKPVPIFLVPTENSIKKNTRPQISSLTQSQ
AETPSGDMHQHEGHIPNAVDSCLQKIFLTVTADLNCNLFSKEQRAYITTLCPSI
RKMEGHDGIEKVCGDFQDIERIHQFLSEQFLESEQKQQFSPSMTERKPLSQQE
RDSCISPSEPETKAEQKSNYFEVPLPYFEYFKYICPDKINSIEKRFGVNIEIQESS
PNMVCLDFTSSRSGDLEAARESFASEFQKNTEPLKQECVSLADSKQANKFKQ
ELNHQFTKLLIKEKGGELTLLGTQDDISAAKQKISEAFVKIPVKLFAANYMMN
VIEVDSAHYKLLETELLQEISEIEKRYDICSKVSEKGQKTCILFESKDRQVDLSV
HAYASFIDAFQHASCQLMREVLLLKSLGKERKHLHQTKFADDFRKRHPNVHF
VLNQESMTLTGLPNHLAKAKQYVLKGGGMSSLAGKKLKEGHETPMDIDSDD
SKAASPPLKGSVSSEASELDKKEKGICVICMDTISNKKVLPKCKHEFCAPCINK
AMSYKPICPTCQTSYGIQKGNQPEGSMVFTVSRDSLPGYESFGTIVITYSMKA
GIQTEEHPNPGKRYPGIQRTAYLPDNKEGRKVLKLLYRAFDQKLIFTVGYSRV
LGVSDVITWNDIHHKTSRFGGPEMYGYPDPSYLKRVKEELKAKGIE

FIGURE 1 cont.

LYMPHOMA ASSOCIATED MOLECULES AND USES THEREFOR

RELATED APPLICATIONS

This application is a continuation application of U.S. patent application Ser. No. 09/957,635, filed on Sep. 19, 2001, which claims priority to U.S. Provisional Application No. 60/233,791, filed on Sep. 19, 2000, the entire contents of each application which are incorporated herein by this reference.

GOVERNMENT FUNDING

Work described herein was supported, at least in part, under grant 1P01 CA66996-01A1 awarded by the NIH. The U.S. government therefore may have certain rights in this invention.

BACKGROUND OF THE INVENTION

The incidence of non-Hodgkin's lymphoma in the United States has increased by 75.1% between 1973 and 1992 (Kosary et al., *SEER Cancer Statistics Review, 1973-1992: Tables and Graphs, National Cancer Institute*, NIH Publication No 96-2789, Bethesda, Md.: NIH 1995), a percentage increase exceeded only by that for prostate cancer, lung cancer in women, and melanoma.

Diffuse large B-cell lymphoma (DLB-CL) is the most common non-Hodgkin's lymphoma in adults. Although DLB-CL is curable in approximately 40% of patients, the majority of patients progress and die of their disease (Shipp et al. Non-Hodgkin's Lymphomas. In DeVita (ed): Principles and Practice of Oncology, 5th Edition, Philadelphia, J. B. Lippincott Company. pp. 2165-2220, 1997). Additional advancements in the treatment of this aggressive but potentially curable non-Hodgkin's lymphoma are likely to require a more precise understanding of the disease's cellular and molecular bases.

A novel gene termed "B-aggressive lymphoma" (BAL), was found to be significantly more abundant in tumors from patients with "high-risk (HR)" (International Prognostic Index, IPI) fatal disease than in tumors from cured "low risk (LR [IPI])" patients.

SUMMARY OF THE INVENTION

To identify other genes which contribute to the observed differences in clinical outcome in DLB-CLs, yeast two-hybrid screens (Zervos et al. (1993) Cell 72:223-232) were used to identify proteins which bind to or interact with the BAL protein. A novel BAL-associated protein termed "B-lymphoma and BAL-associated protein" or "BBAP" has been identified, which specifically interacts with the BAL carboxyl terminal region. The co-association between BBAP and BAL was confirmed by co-transfecting tagged constructs (FLAG-tagged BBAP and HA-tagged BAL) into COS cells, immunoprecipitating BBAP/BAL complexes with a FLAG antibody, blotting the immunoprecipitates, and identifying BAL with an HA antibody. Moreover, paired northern blot analyses of BBAL and BAL transcripts have demonstrated that these genes are expressed at very similar levels in multiple normal tissues and a variety of hematopoietic cell lines.

Accordingly, in one aspect, the present invention provides isolated nucleic acid molecules encoding BBAP proteins or biologically active portions thereof, as well as nucleic acid fragments suitable as primers or hybridization probes for the detection of BBAP-encoding nucleic acids. The BBAP molecules of the present invention are useful as modulating agents for regulating a variety of cellular processes.

In one embodiment, a BBAP nucleic acid molecule of the invention is at least 50%, 55%, 60%, 65%, 70%, 75%, 80%, 85%, 90%, 95%, 96%, 97%, 98%, or more identical to the nucleotide sequence (e.g., to the entire length of the nucleotide sequence) shown in SEQ ID NO:1 or 3.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1-2762 of SEQ ID NO:1. In another embodiment, the nucleic acid molecule includes SEQ ID NO:3 and nucleotides 1-166 or 2384-2762 of SEQ ID NO:1. In another preferred embodiment, the nucleic acid molecule consists of the nucleotide sequence shown in SEQ ID NO:1 or 3.

In another preferred embodiment, the nucleic acid molecule includes a fragment of at least 50, 100, 150, 200, 250, 300, 350, 400, 450, 500, 550, 600, 650, 700, 750 or more nucleotides (e.g., 50, 100, 200, 250 or more contiguous nucleotides) of the nucleotide sequence of SEQ ID NO:1 or 3, or a complement thereof.

In another embodiment, a BBAP nucleic acid molecule includes a nucleotide sequence encoding a protein having an amino acid sequence sufficiently homologous to the amino acid sequence of SEQ ID NO:2. In a preferred embodiment, a BBAP nucleic acid molecule includes a nucleotide sequence encoding a protein having an amino acid sequence at least 50%, 55%, 60%, 65%, 70%, 75%, 80%, 85%, 90%, 95%, 96%, 97%, 98% or more identical to the entire length of the amino acid sequence of SEQ ID NO:2.

In another preferred embodiment, an isolated nucleic acid molecule encodes the amino acid sequence of human BBAP. In yet another preferred embodiment, the nucleic acid molecule includes a nucleotide sequence encoding a protein having the amino acid sequence of SEQ ID NO:2. In yet another preferred embodiment, the nucleic acid molecule is at least 300, 400, 500, or more nucleotides in length. In a further preferred embodiment, the nucleic acid molecule is at least 600, 700, 800, 900, or more nucleotides in length and encodes a protein having a BBAP activity (as described herein).

Another embodiment of the invention features nucleic acid molecules, preferably BBAP nucleic acid molecules, which specifically detect BBAP nucleic acid molecules relative to nucleic acid molecules encoding non-BBAP proteins. For example, in one embodiment, such a nucleic acid molecule is at least 300, 350, 400, 500, 550, 600, or more nucleotides in length and hybridizes under stringent conditions to a nucleic acid molecule comprising the nucleotide sequence shown in SEQ ID NO:1 or 3 or a complement thereof.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or 3 under stringent conditions.

Another embodiment of the invention provides an isolated nucleic acid molecule which is antisense to a BBAP nucleic acid molecule, e.g., the coding strand of a BBAP nucleic acid molecule.

Another aspect of the invention provides a vector comprising a BBAP nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a BBAP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant BBAP proteins and polypeptides. In one embodiment, the isolated protein, preferably a BBAP protein, includes at least one or more of the following domains: a nuclear localization signal or a C3HC4-type zinc finger motif. In a preferred embodiment, a BBAP protein, includes at least one or more of the following domains: a nuclear localization signal or a C3HC4-type zinc finger motif and has an amino acid sequence at least about 50%, 55%, 60%, 65%, 70%, 75%, 80%, 85%, 90%, 95%, 96%, 97%, 98% or more identical to the amino acid sequence of SEQ ID NO:2. In another preferred embodiment, a BBAP protein, includes at least one or more of the following domains: a nuclear localization signal or a C3HC4-type zinc finger motif and plays a role in the pathogenesis of non-Hodgkin's lymphoma. In yet another preferred embodiment, a BBAP protein, includes at least one or more of the following domains: a nuclear localization signal or a C3HC4-type zinc finger motif and is encoded by a nucleic acid molecule having a nucleotide sequence which hybridizes under stringent hybridization conditions to a nucleic acid molecule comprising the nucleotide sequence of SEQ ID NO:1 or 3.

In another embodiment, the invention features BBAP proteins which are produced by recombinant DNA techniques. Alternative to recombinant expression, a BBAP protein or polypeptide can be synthesized chemically using standard peptide synthesis techniques, based on the amino acid sequence of SEQ ID NO:2.

In another embodiment, the invention features fragments of the protein having the amino acid sequence of SEQ ID NO:2, wherein the fragment comprises at least 15 amino acids (e.g., contiguous amino acids) of the amino acid sequence of SEQ ID NO:2. In another embodiment, a BBAP protein has the amino acid sequence of SEQ ID NO:2.

In another embodiment, the invention features an isolated BBAP protein which is encoded by a nucleic acid molecule consisting of a nucleotide sequence at least about 50%, 55%, 60%, 65%, 70%, 75%, 80%, 85%, 90%, 95%, 96%, 97%, 98% or more identical to a nucleotide sequence of SEQ ID NO:1 or 3. This invention further features an isolated BBAP protein which is encoded by a nucleic acid molecule consisting of a nucleotide sequence which hybridizes under stringent hybridization conditions to a nucleic acid molecule comprising the nucleotide sequence of SEQ ID NO:1 or 3.

The proteins of the present invention or portions thereof, e.g., biologically active portions thereof, can be operatively linked to a non-BBAP polypeptide (e.g., heterologous amino acid sequences) to form fusion proteins. The invention further features antibodies, such as monoclonal or polyclonal antibodies, that specifically bind the BBAP proteins of the invention. In addition, the BBAP proteins or biologically active portions thereof can be incorporated into pharmaceutical compositions, which optionally include pharmaceutically acceptable carriers.

In another aspect, the present invention provides a method for detecting the presence of a BBAP nucleic acid molecule, protein or polypeptide in a biological sample by contacting the biological sample with an agent capable of detecting a BBAP nucleic acid molecule, protein or polypeptide such that the presence of a BBAP nucleic acid molecule, protein or polypeptide is detected in the biological sample.

In another aspect, the present invention provides a method for detecting the presence of BBAP activity in a biological sample by contacting the biological sample with an agent capable of detecting an indicator of BBAP activity such that the presence of BBAP activity is detected in the biological sample.

In another aspect, the invention provides a method for modulating BBAP activity comprising contacting a cell capable of expressing BBAP with an agent that modulates BBAP activity such that BBAP activity in the cell is modulated. In one embodiment, the agent inhibits BBAP activity. In another embodiment, the agent stimulates BBAP activity. In one embodiment, the agent is an antibody that specifically binds to a BBAP protein. In another embodiment, the agent modulates expression of BBAP by modulating transcription of a BBAP gene or translation of a BBAP mRNA. In yet another embodiment, the agent is a nucleic acid molecule having a nucleotide sequence that is antisense to the coding strand of a BBAP mRNA or a BBAP gene.

In one embodiment, the methods of the present invention are used to treat a subject having a disorder characterized by aberrant BBAP protein or nucleic acid expression or activity, e.g., non-Hodgkin's lymphoma, by administering an agent which is a BBAP modulator to the subject. In one embodiment, the BBAP modulator is a BBAP protein. In another embodiment the BBAP modulator is a BBAP nucleic acid molecule. In yet another embodiment, the BBAP modulator is a peptide, peptidomimetic, or other small molecule. In a preferred embodiment, the disorder characterized by aberrant BBAP protein or nucleic acid expression is a proliferative disorder, e.g., non-Hodgkin's lymphoma.

The present invention also provides a diagnostic assay for identifying the presence or absence of a genetic alteration characterized by at least one of (i) aberrant modification or mutation of a gene encoding a BBAP protein; (ii) mis-regulation of the gene; and (iii) aberrant post-translational modification of a BBAP protein, wherein a wild-type form of the gene encodes a protein with a BBAP activity.

In another aspect the invention provides a method for producing or identifying a compound that binds to or modulates the activity of a BBAP protein, by providing an indicator composition comprising a BBAP protein having BBAP activity, contacting the indicator composition with a test compound, and determining the effect of the test compound on BBAP activity in the indicator composition to produce or identify a compound that modulates the activity of a BBAP protein.

Other features and advantages of the invention will be apparent from the following detailed description and claims.

BRIEF DESCRIPTION OF THE DRAWINGS

FIG. 1 depicts the cDNA sequence and predicted amino acid sequence of human BBAP. The nucleotide sequence corresponds to nucleic acids 1 to 2762 of SEQ ID NO:1. The amino acid sequence corresponds to amino acids 1 to 739 of SEQ ID NO: 2. The coding region without the 5' and 3' untranslated regions of the human BBAP gene is shown in SEQ ID NO:3.

DETAILED DESCRIPTION OF THE INVENTION

Figure 2:
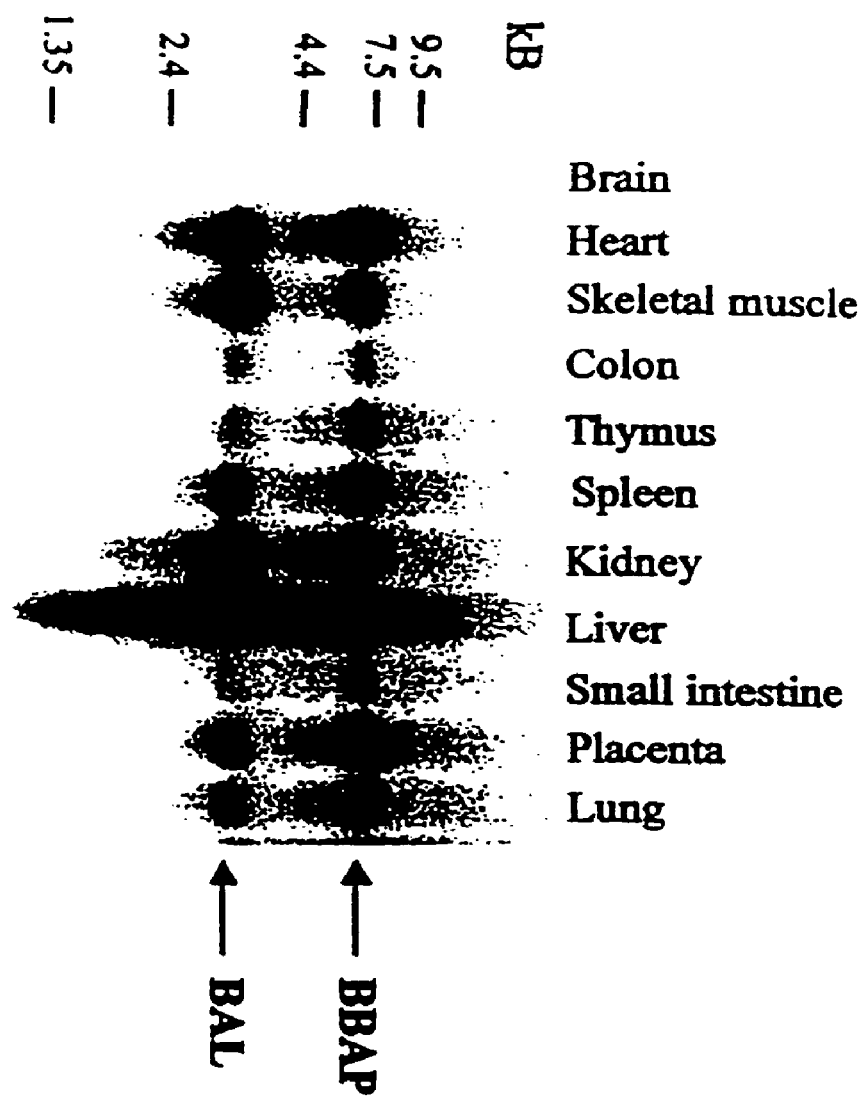
FIG. 2 depicts the results from a paired northern blot analysis of BBAP and BAL transcripts, which indicate that these genes are expressed at very similar levels in multiple normal tissues.

The present invention is based, at least in part, on the discovery of novel molecules, referred to herein as BBAP nucleic acid and protein molecules. The BBAP proteins of the present invention bind to or interact with the BAL molecules which are differentially expressed in malignancies such as lymphoma, e.g., non-Hodgkin's lymphoma. The newly identified BBAP nucleic acid and protein molecules can be used to identify cells exhibiting or predisposed to a malignancy such as lymphoma, e.g., non-Hodgkin's lymphoma, thereby diagnosing subjects having, or prone to developing such disorders.

As used herein, a "malignancy" includes a cancerous uncontrolled growth of cells in an area of the body. Malignant cancers are typically classified by their microscopic appearance and the type of tissue from which they arise. Examples of malignancies include carcinomas, sarcomas, myelomas, chondrosarcomas, adenosarcomas, angiosarcomas, neuroblastomas, gliomas, medulloblastomas, erythroleukemias, and myelogenous leukemias.

As used herein, a "lymphoma" includes a malignant neoplastic disorder of lymphoreticular tissue which produces a distinct tumor mass. Lymphomas include tumors derived from the lymphoid lineage. Lymphomas usually arise in lymph nodes, the spleen, or other areas rich in lymphoid tissue. Lymphomas are typically subclassified as Hodgkin's disease and Non-Hodgkin's lymphomas, e.g., Burkitt's lymphoma, large-cell lymphoma, and follicular lymphoma.

As used herein, "differential expression" or differentially expressed" includes both quantitative as well as qualitative differences in the temporal and/or cellular expression pattern of a gene, e.g., the BBAP gene, among, for example, normal cells and cells from patients with "high risk" fatal diffuse large B-cell lymphoma (DLB-CL) or "low risk" cured DLB-CL. Genes which are differentially expressed can be used as part of a prognostic or diagnostic marker for the evaluation of subjects at risk for developing a malignancy such as a lymphoma, e.g., non-Hodgkin's lymphoma. Depending on the expression level of the gene, the progression state or the aggressiveness of the disorder can be evaluated. Methods for detecting the differential expression of a gene are described herein.

The BBAP molecules comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of BBAP proteins comprise at least one "nuclear localization signal." As used herein, the term "nuclear localization signal" includes an amino acid sequence of about 4-20 amino acid residues in length, which serves to direct a protein to the nucleus. Typically, the nuclear localization sequence is rich in basic amino acids. A nuclear localization signal may have one or more of the following sequences: RKRH (SEQ ID NO:5); PRVRRKL (SEQ ID NO:6); or RKHLHQTKFADDFRKRH (SEQ ID NO:7). Nuclear localization signals are described in, for example, Gorlich D. (1998) EMBO 5.17:2721-7, the contents of which are incorporated herein by reference. Amino acid residues 20-26, 462-478, and 475-478 of the human BBAP comprise nuclear localization signals.

In another embodiment, a BBAP protein of the present invention is identified based on the presence of at least one "C3HC4-type zinc finger motif" in the protein or corresponding nucleic acid molecule. As used herein, the term "C3HC4-type zinc finger motif" includes an amino acid sequence of about 40-70 amino acid residues in length and having the general sequence C-X-(I,V)-C-X(11-30)-C-X-H-X-(F,I,L)-C-X(2)-C-X-(I,L,M)-X(10-18)-C-P-X-C (SEQ ID NO:4) (where X can be any amino acid). Proteins comprising a ring-H$_2$-finger motif are believed to interact with DNA and to be involved in diverse functions, including site specific recombination, DNA repair, and transcriptional regulation. The ring-H$_2$-finger may also bind zinc/divalent metal ions to form a structure that is involved in specific protein-protein interactions (similar to the zinc-cysteine clusters of the adenovirus E1A). Amino acid residues 561-599 of the human BBAP comprise a C3HC4-type zinc finger motif.

Isolated BBAP proteins of the invention have an amino acid sequence sufficiently homologous to the amino acid sequence of SEQ ID NO:2 or are encoded by a nucleotide sequence sufficiently homologous to SEQ ID NO:1 or 3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50%, preferably 60% identity, more preferably 70%-80%, and even more DFN-036 preferably 90-95% identity across the amino acid sequences of the domains are defined herein as sufficiently identical. Furthermore, amino acid or nucleotide sequences which share at least 30%, 40%, or 50%, preferably 60%, more preferably 70-80%, or 90-95% identity and share a common functional activity are defined herein as sufficiently identical.

As used interchangeably herein, "BBAP activity", "biological activity of BBAP" or "functional activity of BBAP", refers to an activity exerted by a BBAP protein, polypeptide or nucleic acid molecule on a BBAP responsive cell or on a BBAP protein substrate, as determined in vivo, ex vivo, or in vitro, according to standard techniques. In one embodiment, a BBAP activity is a direct activity, such as an association with a BBAP-target molecule, e.g., a BAL molecule. As used herein, a "target molecule" or "binding partner" is a molecule with which a BBAP protein binds or interacts in nature, such that BBAP-mediated function is achieved. A BBAP target molecule can be a non-BBAP molecule such as a BAL molecule. In an exemplary embodiment, a BBAP target molecule is a BBAP ligand. Alternatively, a BBAP activity is an indirect activity, such as a cellular signaling activity mediated by interaction of the BBAP protein with a BBAP ligand. BBAP activities include modulation of cellular adhesion and modulation of the aggressiveness or severity of a malignancy such as DLB-CL. BBAP activities are described herein.

Accordingly, another embodiment of the invention features isolated BBAP proteins and polypeptides having a BBAP activity. Preferred proteins are BBAP proteins having at least one or more of the following domains: a nuclear localization signal or a C3HC4-type zinc finger motif and, preferably, a BBAP activity.

The nucleotide sequence of the isolated human BBAP cDNA and the predicted amino acid sequence of the human BBAP polypeptide are shown in FIG. 1 and in SEQ ID NOS:1 and 2, respectively.

The human BBAP gene, which is approximately 2762 nucleotides in length, encodes a protein having a molecular weight of approximately 83.6 kD and which is approximately 739 amino acid residues in length.

Various aspects of the invention are described in further detail in the following subsections:

I. Isolated Nucleic Acid Molecules

One aspect of the invention pertains to isolated nucleic acid molecules that encode BBAP proteins or biologically active portions thereof, as well as nucleic acid fragments sufficient for use as hybridization probes to identify BBAP-encoding nucleic acid molecules (e.g., BBAP mRNA) and fragments for use as PCR primers for the amplification or mutation of BBAP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BBAP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3 or a portion thereof, can be isolated using standard molecular biology techniques and the sequence information provided herein. Using all or portion of the nucleic acid sequence of SEQ ID NO:1 or 3, as a hybridization probe, BBAP nucleic acid molecules can be isolated using standard hybridization and cloning techniques (e.g., as described in Sambrook, J., Fritsh, E. F., and Maniatis, T. *Molecular Cloning. A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to BBAP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human BBAP cDNA. This cDNA comprises sequences encoding the human BBAP protein (i.e., "the coding region", from nucleotides 167-2383), as well as 5' untranslated sequences (nucleotides 1-166) and 3' untranslated sequences (nucleotides 2384-2762). Alternatively, the nucleic acid molecule can comprise only the coding region of SEQ ID NO:1 (e.g., nucleotides 167-2383, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3, such that it can hybridize to the nucleotide sequence shown in SEQ ID NO:1 or 3.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98% or more identical to the entire length of the nucleotide sequence shown in SEQ ID NO:1 or 3 or a portion of any of these nucleotide sequences.

Moreover, the nucleic acid molecule of the invention can comprise only a portion of the nucleic acid sequence of SEQ ID NO:1 or 3, for example, a fragment which can be used as a probe or primer or a fragment encoding a portion of a BBAP protein, e.g., a biologically active portion of a BBAP protein. The nucleotide sequence determined from the cloning of the BBAP gene allows for the generation of probes and primers designed for use in identifying and/or cloning other BBAP family members, as well as BBAP homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3, of an anti-sense sequence of SEQ ID NO:1 or 3, or of a naturally occurring allelic variant or mutant of SEQ ID NO:1 or 3. In an exemplary embodiment, a nucleic acid molecule of the present invention comprises a nucleotide sequence which is greater than 300-350, 350-400, 400-450, 452, 452-500, 500-550, 550-600, 607, 607-650, 650-700, 700-750, 750-800, 800-850, 850-900, 900-950, 950-1000, or more nucleotides in length and hybridizes under stringent hybridization conditions to a nucleic acid molecule of SEQ ID NO:1 or 3. Ranges intermediate to the above-recited values are also intended to be part of this invention. For example, ranges using any combination of the above recited values as upper and/or lower limits are intended to be included.

Probes based on the BBAP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BBAP protein, such as by measuring a level of a BBAP-encoding nucleic acid in a sample of cells from a subject e.g., detecting BBAP mRNA levels or determining whether a genomic BBAP gene has been mutated or deleted.

A nucleic acid fragment encoding a "biologically active portion of a BBAP protein" can be prepared by isolating a portion of the nucleotide sequence of SEQ ID NO:1 or 3, which encodes a polypeptide having a BBAP biological activity (the biological activities of the BBAP proteins are described herein), expressing the encoded portion of the BBAP protein (e.g., by recombinant expression in vitro) and assessing the activity of the encoded portion of the BBAP protein.

The invention further encompasses nucleic acid molecules that differ from the nucleotide sequence shown in SEQ ID NO:1 or 3, due to degeneracy of the genetic code and thus encode the same BBAP proteins as those encoded by the nucleotide sequence shown in SEQ ID NO:1 or 3. In another embodiment, an isolated nucleic acid molecule of the invention has a nucleotide sequence encoding a protein having an amino acid sequence shown in SEQ ID NO:2.

In addition to the BBAP nucleotide sequences shown in SEQ ID NO:1 or 3, it will be appreciated by those skilled in the art that DNA sequence polymorphisms that lead to changes in the amino acid sequences of the BBAP proteins may exist within a population (e.g., the human population). Such genetic polymorphism in the BBAP genes may exist among individuals within a population due to natural allelic variation. As used herein, the terms "gene" and "recombinant gene" refer to nucleic acid molecules which include an open reading frame encoding a BBAP protein, preferably a mammalian BBAP protein, and can further include non-coding regulatory sequences, and introns.

Allelic variants of human BBAP include both functional and non-functional BBAP proteins. Functional allelic variants are naturally occurring amino acid sequence variants of the human BBAP protein that maintain the ability to bind a BBAP ligand and/or modulate the occurrence or severity of a malignancy such as a lymphoma, e.g., non-Hodgkin's lymphoma. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human BBAP protein that do not have the ability to either bind a BBAP ligand and/or modulate occurrence or severity of a malignancy such as a lymphoma, e.g., non-Hodgkin's lymphoma. Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human BBAP protein. Orthologues of the human BBAP protein are proteins that are isolated from non-human organisms and possess the same BBAP ligand binding and/or modulation of the occurrence or severity of a malignancy such as a lymphoma, e.g., non-Hodgkin's lymphoma capabilities of the human BBAP protein. Orthologues of the human BBAP protein can readily be identified as comprising an amino acid sequence that is substantially homologous to SEQ ID NO:2.

Moreover, nucleic acid molecules encoding other BBAP family members and, thus, which have a nucleotide sequence which differs from the BBAP sequences of SEQ ID NO:1 or 3 are intended to be within the scope of the invention. For example, another BBAP cDNA can be identified based on the nucleotide sequence of human BBAP. Moreover, nucleic acid molecules encoding BBAP proteins from different species, and which, thus, have a nucleotide sequence which differs from the BBAP sequences of SEQ ID NO:1 or 3 are intended to be within the scope of the invention. For example, a monkey or murine BBAP cDNA can be identified based on the nucleotide sequence of a human BBAP.

Nucleic acid molecules corresponding to natural allelic variants and homologues of the BBAP cDNAs of the invention can be isolated based on their homology to the BBAP nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the BBAP cDNAs of the invention can further be isolated by mapping to the same chromosome or locus as the BBAP gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 30, 50, 100, 150, 200, 250, 300, 350, 400, 450, 452, 500, 550, 607, 600, 650, 700, 750, 800, 850, 900, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the BBAP sequences that may exist in the population, the skilled artisan will further appreciate that changes can be introduced by mutation into the nucleotide sequences of SEQ ID NO:1 or 3 thereby leading to changes in the amino acid sequence of the encoded BBAP proteins, without altering the functional ability of the BBAP proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of BBAP (e.g., the sequence of SEQ ID NO:2) without altering the biological activity, whereas an "essential" amino acid residue is required for biological activity. For example, amino acid residues that are conserved among the BBAP proteins of the present invention, are predicted to be particularly unamenable to alteration. Furthermore, additional amino acid residues that are conserved between the BBAP proteins of the present invention and other members of the BBAP family are not likely to be amenable to alteration.

Accordingly, another aspect of the invention pertains to nucleic acid molecules encoding BBAP proteins that contain changes in amino acid residues that are not essential for activity. Such BBAP proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98% or more homologous to SEQ ID NO:2.

An isolated nucleic acid molecule encoding a BBAP protein homologous to the protein of SEQ ID NO:2 can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BBAP protein is preferably replaced with another amino acid residue from the same side chain family. Alternatively, in another embodiment, mutations can be introduced randomly along all or part of a BBAP coding sequence, such as by saturation mutagenesis, and the resultant mutants can be screened for BBAP biological activity to identify mutants that retain activity. Following mutagenesis of SEQ ID NO:1 or 3, the encoded protein can be expressed recombinantly and the activity of the protein can be determined.

In a preferred embodiment, a mutant BBAP protein can be assayed for the ability to (1) interact with a non-BBAP protein molecule, e.g., BAL, (2) activate a BBAP-dependent signal transduction pathway, (3) modulate the occurrence or severity of a lymphoma, e.g., non Hodgkin's lymphoma, (4) bind zinc, (5) bind DNA, (6) localize to the nucleus, or (7) modulate the migration of malignant cells, e.g., B-lymphoma cells.

In addition to the nucleic acid molecules encoding BBAP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire BBAP coding strand, or to only a portion thereof. In one embodiment, an antisense nucleic acid molecule is antisense to a "coding region" of the coding strand of a nucleotide sequence encoding BBAP. The term "coding region" refers to the region of the nucleotide sequence comprising codons which are translated into amino acid residues (e.g., the coding region of human and murine BBAP corresponds to SEQ ID NO:3). In another embodiment, the antisense nucleic acid molecule is antisense to a "noncoding region" of the coding strand of a nucleotide sequence encoding BBAP. The term "noncoding region" refers to 5' and 3' sequences which flank the coding region that are not translated into amino acids (i.e., also referred to as 5' and 3' untranslated regions).

Given the coding strand sequences encoding BBAP disclosed herein (e.g., SEQ ID NO:3), antisense nucleic acids of the invention can be designed according to the rules of Watson and Crick base pairing. The antisense nucleic acid molecule can be complementary to the entire coding region of BBAP mRNA, but more preferably is an oligonucleotide which is antisense to only a portion of the coding or noncoding region of BBAP mRNA. For example, the antisense oligonucleotide can be complementary to the region surrounding the translation start site of BBAP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galaciosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BBAP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave BBAP mRNA transcripts to thereby inhibit translation of BBAP mRNA. A ribozyme having specificity for a BBAP-encoding nucleic acid can be designed based upon the nucleotide sequence of a BBAP cDNA disclosed herein (i.e., SEQ ID NO:1 or 3). For example, a derivative of a Tetrahymena L-19 IVS RNA can be constructed in which the nucleotide sequence of the active site is complementary to the nucleotide sequence to be cleaved in a BBAP-encoding mRNA. See, e.g., Cech et al. U.S. Pat. No. 4,987,071; and Cech et al. U.S. Pat. No. 5,116,742. Alternatively, BBAP mRNA can be used to select a catalytic RNA having a specific ribonuclease activity from a pool of RNA molecules. See, e.g., Bartel, D. and Szostak, J. W. (1993) *Science* 261:1411-1418.

Alternatively, BBAP gene expression can be inhibited by targeting nucleotide sequences complementary to the regulatory region of the BBAP (e.g., the BBAP promoter and/or enhancers) to form triple helical structures that prevent transcription of the BBAP gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) Bioassays 14(12):807-15.

In yet another embodiment, the BBAP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of BBAP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of BBAP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of BBAP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of BBAP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

II. Isolated BBAP Proteins and Anti-BBAP Antibodies

One aspect of the invention pertains to isolated BBAP proteins, and biologically active portions thereof, as well as polypeptide fragments suitable for use as immunogens to raise anti-BBAP antibodies. In one embodiment, native BBAP proteins can be isolated from cells or tissue sources by an appropriate purification scheme using standard protein purification techniques. In another embodiment, BBAP proteins are produced by recombinant DNA techniques. Alternative to recombinant expression, a BBAP protein or polypeptide can be synthesized chemically using standard peptide synthesis techniques.

An "isolated" or "purified" protein or biologically active portion thereof is substantially free of cellular material or other contaminating proteins from the cell or tissue source from which the BBAP protein is derived, or substantially free from chemical precursors or other chemicals when chemically synthesized. The language "substantially free of cellular material" includes preparations of BBAP protein in which the protein is separated from cellular components of the cells from which it is isolated or recombinantly produced. In one embodiment, the language "substantially free of cellular material" includes preparations of BBAP protein having less than about 30% (by dry weight) of non-BBAP protein (also referred to herein as a "contaminating protein"), more preferably less than about 20% of non-BBAP protein, still more preferably less than about 10% of non-BBAP protein, and most preferably less than about 5% non-BBAP protein. When the BBAP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BBAP protein in which the protein is separated from chemical precursors or other chemicals which are involved in the synthesis of the protein. In one embodiment, the language "substantially free of chemical precursors or other chemicals" includes preparations of BBAP protein having less than about 30% (by dry weight) of chemical precursors or non-BBAP chemicals, more preferably less than about 20% chemical precursors or non-BBAP chemicals, still more preferably less than about 10% chemical precursors or non-BBAP chemicals, and most preferably less than about 5% chemical precursors or non-BBAP chemicals.

As used herein, a "biologically active portion" of a BBAP protein includes a fragment of a BBAP protein which participates in an interaction between a BBAP molecule and a non-BBAP molecule. Biologically active portions of a BBAP protein include peptides comprising amino acid sequences sufficiently homologous to or derived from the amino acid sequence of the BBAP protein, e.g., the amino acid sequence shown in SEQ ID NO:2, which include less amino acids than the full length BBAP proteins, and exhibit at least one activity of a BBAP protein. Typically, biologically active portions comprise a domain or motif with at least one activity of the BBAP protein, e.g., modulating cellular adhesion. A biologically active portion of a BBAP protein can be a polypeptide which is, for example, 10, 25, 50, 100, 200 or more amino acids in length. Biologically active portions of a BBAP protein can be used as targets for developing agents which modulate a BBAP mediated activity, e.g., the occurrence or severity of a lymphoma, e.g., non-Hodgkin's lymphoma.

In one embodiment, a biologically active portion of a BBAP protein comprises at least one nuclear localization signal and/or at least one C3HC4-type zinc finger motif. It is to be understood that a preferred biologically active portion of a BBAP protein of the present invention may contain at least one of the above-identified structural domains. A more preferred biologically active portion of a BBAP protein may contain at least two of the above-identified structural domains. Moreover, other biologically active portions, in which other regions of the protein are deleted, can be prepared by recombinant techniques and evaluated for one or more of the functional activities of a native BBAP protein.

In a preferred embodiment, the BBAP protein has an amino acid sequence shown in SEQ ID NO:2. In other embodiments, the BBAP protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the BBAP protein is a protein which comprises an amino acid sequence at least about 50%, 55%, 60%, 65%, 70%, 75%, 80%, 85%, 90%, 95%, 96%, 97%, 98% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the BBAP amino acid sequence of SEQ ID NO:2 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at the Genetics Computer Group website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the Genetics Computer Group website), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to BBAP nucleic acid molecules of the invention. BLAST protein searches can be performed with the XBLAST program, score=50, wordlength=3 to obtain amino acid sequences homologous to BBAP protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See the NCBI website.

The invention also provides BBAP chimeric or fusion proteins. As used herein, a BBAP "chimeric protein" or "fusion protein" comprises a BBAP polypeptide operatively linked to a non-BBAP polypeptide. An "BBAP polypeptide" refers to a polypeptide having an amino acid sequence corresponding to BBAP, whereas a "non-BBAP polypeptide" refers to a polypeptide having an amino acid sequence corresponding to a protein which is not substantially homologous to the BBAP protein, e.g., a protein which is different from the BBAP protein and which is derived from the same or a different organism. Within a BBAP fusion protein the BBAP polypeptide can correspond to all or a portion of a BBAP protein. In a preferred embodiment, a BBAP fusion protein comprises at least one biologically active portion of a BBAP protein. In another preferred embodiment, a BBAP fusion protein comprises at least two biologically active portions of a BBAP protein. Within the fusion protein, the term "operatively linked" is intended to indicate that the BBAP polypeptide and the non-BBAP polypeptide are fused in-frame to each other. The non-BBAP polypeptide can be fused to the N-terminus or C-terminus of the BBAP polypeptide.

For example, in one embodiment, the fusion protein is a GST-BBAP fusion protein in which the BBAP sequences are fused to the C-terminus of the GST sequences. Such fusion proteins can facilitate the purification of recombinant BBAP.

In another embodiment, the fusion protein is a BBAP protein containing a heterologous signal sequence at its N-terminus. In certain host cells (e.g., mammalian host cells), expression and/or secretion of BBAP can be increased through use of a heterologous signal sequence.

The BBAP fusion proteins of the invention can be incorporated into pharmaceutical compositions and administered to a subject in vivo. The BBAP fusion proteins can be used to affect the bioavailability of a BBAP substrate. Use of BBAP fusion proteins may be useful therapeutically for the treatment of disorders caused by, for example, (i) aberrant modification or mutation of a gene encoding a BBAP protein; (ii) mis-regulation of the BBAP gene; and (iii) aberrant post-translational modification of a BBAP protein.

Moreover, the BBAP-fusion proteins of the invention can be used as immunogens to produce anti-BBAP antibodies in a subject, to purify BBAP ligands and in screening assays to identify molecules which inhibit the interaction of BBAP with a BBAP substrate.

Preferably, a BBAP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An BBAP-encoding nucleic acid can be cloned into such an expression vector such that the fusion moiety is linked in-frame to the BBAP protein.

The present invention also pertains to variants of the BBAP proteins which function as either BBAP agonists (mimetics) or as BBAP antagonists. Variants of the BBAP proteins can be generated by mutagenesis, e.g., discrete point mutation or truncation of a BBAP protein. An agonist of the BBAP proteins can retain substantially the same, or a subset, of the biological activities of the naturally occurring form of a BBAP protein. An antagonist of a BBAP protein can inhibit one or more of the activities of the naturally occurring form of the BBAP protein by, for example, competitively modulating a BBAP-mediated activity of a BBAP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the BBAP protein.

In one embodiment, variants of a BBAP protein which function as either BBAP agonists (mimetics) or as BBAP antagonists can be identified by screening combinatorial libraries of mutants, e.g., truncation mutants, of a BBAP protein for BBAP protein agonist or antagonist activity. In one embodiment, a variegated library of BBAP variants is generated by combinatorial mutagenesis at the nucleic acid level and is encoded by a variegated gene library. A variegated library of BBAP variants can be produced by, for example, enzymatically ligating a mixture of synthetic oligonucleotides into gene sequences such that a degenerate set of potential BBAP sequences is expressible as individual polypeptides, or alternatively, as a set of larger fusion proteins (e.g., for phage display) containing the set of BBAP sequences therein. There are a variety of methods which can be used to produce libraries of potential BBAP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential BBAP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a BBAP protein coding sequence can be used to generate a variegated population of BBAP fragments for screening and subsequent selection of variants of a BBAP protein. In one embodiment, a library of coding sequence fragments can be generated by treating a double stranded PCR fragment of a BBAP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the BBAP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of BBAP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify BBAP variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated BBAP library. For example, a library of expression vectors can be transfected into a cell line which ordinarily responds to a particular ligand in a BBAP-dependent manner. The transfected cells are then contacted with the ligand and the effect of expression of the mutant on signaling by the ligand can be detected, e.g., by measuring cell survival or the activity of a BBAP-regulated transcription factor. Plasmid DNA can then be recovered from the cells which score for inhibition, or alternatively, potentiation of signaling by the ligand, and the individual clones further characterized.

An isolated BBAP protein, or a portion or fragment thereof, can be used as an immunogen to generate antibodies that bind BBAP using standard techniques for polyclonal and monoclonal antibody preparation. A full-length BBAP protein can be used or, alternatively, the invention provides antigenic peptide fragments of BBAP for use as immunogens. The antigenic peptide of BBAP comprises at least 8 amino acid residues of the amino acid sequence shown in SEQ ID NO:2 and encompasses an epitope of BBAP such that an antibody raised against the peptide forms a specific immune complex with BBAP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of BBAP that are located on the surface of the protein, e.g., hydrophilic regions, as well as regions with high antigenicity.

A BBAP immunogen typically is used to prepare antibodies by immunizing a suitable subject, (e.g., rabbit, goat, mouse or other mammal) with the immunogen. An appropriate immunogenic preparation can contain, for example, recombinantly expressed BBAP protein or a chemically synthesized BBAP polypeptide. The preparation can further include an adjuvant, such as Freund's complete or incomplete adjuvant, or similar immunostimulatory agent. Immunization of a suitable subject with an immunogenic BBAP preparation induces a polyclonal anti-BBAP antibody response.

Accordingly, another aspect of the invention pertains to anti-BBAP antibodies. The term "antibody" as used herein refers to immunoglobulin molecules and immunologically active portions of immunoglobulin molecules, i.e., molecules that contain an antigen binding site which specifically binds (immunoreacts with) an antigen, such as BBAP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind BBAP. The term "monoclonal antibody" or "monoclonal antibody composition", as used herein, refers to a population of antibody molecules that contain only one species of an antigen binding site capable of immunoreacting with a particular epitope of BBAP. A monoclonal antibody composition thus typically displays a single binding affinity for a particular BBAP protein with which it immunoreacts.

Polyclonal anti-BBAP antibodies can be prepared as described above by immunizing a suitable subject with a BBAP immunogen. The anti-BBAP antibody titer in the immunized subject can be monitored over time by standard techniques, such as with an enzyme linked immunosorbent assay (ELISA) using immobilized BBAP. If desired, the antibody molecules directed against BBAP can be isolated from the mammal (e.g., from the blood) and further purified by well known techniques, such as protein A chromatography to obtain the IgG fraction. At an appropriate time after immunization, e.g., when the anti-BBAP antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 0.255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a BBAP immunogen as described above, and the culture supernatants of the resulting hybridoma cells are screened to identify a hybridoma producing a monoclonal antibody that binds BBAP.

Any of the many well known protocols used for fusing lymphocytes and immortalized cell lines can be applied for the purpose of generating an anti-BBAP monoclonal antibody (see, e.g., G. Galfre et al. (1977) *Nature* 266:55052; Gefter et al. *Somatic Cell Genet.*, cited supra; Lerner, *Yale J.*

Biol. Med., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind BBAP, e.g., using a standard ELISA assay.

Alternative to preparing monoclonal antibody-secreting hybridomas, a monoclonal anti-BBAP antibody can be identified and isolated by screening a recombinant combinatorial immunoglobulin library (e.g., an antibody phage display library) with BBAP to thereby isolate immunoglobulin library members that bind BBAP. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-BBAP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-BBAP antibody (e.g., monoclonal antibody) can be used to isolate BBAP by standard techniques, such as affinity chromatography or immunoprecipitation. An anti-BBAP antibody can facilitate the purification of natural BBAP from cells and of recombinantly produced BBAP expressed in host cells. Moreover, an anti-BBAP antibody can be used to detect BBAP protein (e.g., in a cellular lysate or cell supernatant) in order to evaluate the abundance and pattern of expression of the BBAP protein. Anti-BBAP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a BBAP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology. Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., BBAP proteins, mutant forms of BBAP proteins, fusion proteins, and the like).

The recombinant expression vectors of the invention can be designed for expression of BBAP proteins in prokaryotic or eukaryotic cells. For example, BBAP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in BBAP activity assays, (e.g., direct assays or competitive assays described in detail below), or to generate antibodies specific for BBAP proteins, for example. In a preferred embodiment, a BBAP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the BBAP expression vector is a yeast expression vector. Examples of vectors for expression in yeast *S. cerivisae* include pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, BBAP proteins can be expressed in insect cells using baculovirus expression vectors. Baculovirus vectors available for expression of proteins in cultured insect cells (e.g., Sf 9 cells) include the pAc series (Smith et al. (1983) *Mol. Cell. Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to BBAP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a BBAP nucleic acid molecule of the invention is introduced, e.g., a BBAP nucleic acid molecule within a recombinant expression vector or a BBAP nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a BBAP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a BBAP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a BBAP protein. Accordingly, the invention further provides methods for producing a BBAP protein using the host cells of the invention. In one embodiment, the method comprises culturing the host cell of invention (into which a recombinant expression vector encoding a BBAP protein has been introduced) in a suitable medium such that a BBAP protein is produced. In another embodiment, the method further comprises isolating a BBAP protein from the medium or the host cell.

The host cells of the invention can also be used to produce non-human transgenic animals. For example, in one embodiment, a host cell of the invention is a fertilized oocyte or an embryonic stem cell into which BBAP-coding sequences have been introduced. Such host cells can then be used to create non-human transgenic animals in which exogenous BBAP sequences have been introduced into their genome or homologous recombinant animals in which endogenous BBAP sequences have been altered. Such animals are useful for studying the function and/or activity of a BBAP and for identifying and/or evaluating modulators of BBAP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BBAP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a BBAP-encoding nucleic acid into the male pronuclei of a fertilized oocyte, e.g., by microinjection, retroviral infection, and allowing the oocyte to develop in a pseudopregnant female foster animal. The BBAP cDNA sequence of SEQ ID NO:1 can be introduced as a transgene into the genome of a non-human animal. Alternatively, a nonhuman homologue of a human BBAP gene, such as a mouse or rat BBAP gene, can be used as a transgene. Alternatively, a BBAP gene homologue, can be isolated based on hybridization to the BBAP cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to a BBAP transgene to direct expression of a BBAP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a BBAP transgene in its genome and/or expression of BBAP mRNA in tissues or cells of the animals. A transgenic founder animal can then be used to breed additional animals carrying the transgene. Moreover, transgenic animals carrying a transgene encoding a BBAP protein can further be bred to other transgenic animals carrying other transgenes.

To create a homologous recombinant animal, a vector is prepared which contains at least a portion of a BBAP gene into which a deletion, addition or substitution has been introduced to thereby alter, e.g., functionally disrupt, the BBAP gene. The BBAP gene can be a human gene (e.g., the cDNA of SEQ ID NO:3), but more preferably, is a non-human homologue of a human BBAP gene. For example, a mouse BBAP gene can be used to construct a homologous recombination nucleic acid molecule, e.g., a vector, suitable for altering an endogenous BBAP gene in the mouse genome. In a preferred embodiment, the homologous recombination nucleic acid molecule is designed such that, upon homologous recombination, the endogenous BBAP gene is functionally disrupted (i.e., no longer encodes a functional protein; also referred to as a "knock out" vector). Alternatively, the homologous recombination nucleic acid molecule can be designed such that, upon homologous recombination, the endogenous BBAP gene is mutated or otherwise altered but still encodes functional protein (e.g., the upstream regulatory region can be altered to thereby alter the expression of the endogenous BBAP protein). In the homologous recombination nucleic acid molecule, the altered portion of the BBAP gene is flanked at its 5' and 3' ends by additional nucleic acid sequence of the BBAP gene to allow for homologous recombination to occur between the exogenous BBAP gene carried by the homologous recombination nucleic acid molecule and an endogenous BBAP gene in a cell, e.g., an embryonic stem cell. The additional flanking BBAP nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced BBAP gene has homologously recombined with the endogenous BBAP gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage PI. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The BBAP nucleic acid molecules, fragments of BBAP proteins, and anti-BBAP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a BBAP protein or an anti-BBAP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a BBAP protein of the invention has one or more of the following activities: (1) it interacts with a non-BBAP protein molecule, e.g., BAL; (2) it activates a BBAP-dependent signal transduction pathway; (3) it modulates the occurrence and severity of a malignancy such as a lymphoma, e.g., non-Hodgkin's lymphoma; (4) it modulates cell migration, motility, and shape, as well as cell/cell and cell/extra-cellular matrix interactions; (5) it modulates the activity of E47, and (6) it modulates the degradation of non-BBAP proteins (e.g., BAL) by, for example, modifying these proteins and targeting them to the proteoliposome and, thus, can be used to, for example, (1) modulate the interaction with a non-BBAP protein molecule, e.g., BAL; (2) activate a BBAP-dependent signal transduction pathway; (3) modulate the occurrence and severity of a malignancy such as a lymphoma, e.g., non-Hodgkin's lymphoma; (4) modulate cell migration, motility, and shape, as well as cell/cell and cell/extra-cellular matrix interactions; (5) modulate the activity of E47, and/or (6) modulate the degradation of non-BBAP proteins (e.g., BAL) by, for example, modifying these proteins and targeting them to the proteoliposome.

The isolated nucleic acid molecules of the invention can be used, for example, to express BBAP protein (e.g., via a recombinant expression vector in a host cell in gene therapy applications), to detect BBAP mRNA (e.g., in a biological sample) or a genetic alteration in a BBAP gene, and to modulate BBAP activity, as described further below. The BBAP proteins can be used to treat disorders characterized by insufficient or excessive production of a BBAP substrate or production of BBAP inhibitors. In addition, the BBAP proteins can be used to screen for naturally occurring BBAP substrates, to screen for drugs or compounds which modulate BBAP activity, as well as to treat disorders characterized by insufficient or excessive production of BBAP protein or production of BBAP protein forms which have decreased or aberrant activity compared to BBAP wild type protein (e.g., Non-Hodgkin's lymphoma). Moreover, the anti-BBAP antibodies of the invention can be used to detect and isolate BBAP proteins, regulate the bioavailability of BBAP proteins, and modulate BBAP activity.

A. Screening Assays:

The invention provides a method (also referred to herein as a "screening assay") for identifying and/or producing modulators, i.e., candidate or test compounds or agents (e.g., peptides, peptidomimetics, small molecules or other drugs) which bind to BBAP proteins, have a stimulatory or inhibitory effect on, for example, BBAP expression or BBAP activity, or have a stimulatory or inhibitory effect on, for example, the expression or activity of a BBAP substrate.

In one embodiment, the invention provides assays for screening candidate or test compounds which are substrates of a BBAP protein or polypeptide or biologically active portion thereof. In another embodiment, the invention provides assays for screening candidate or test compounds which bind to or modulate the activity of a BBAP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a BBAP protein or biologically active portion thereof is contacted with a test compound and the ability of the test compound to modulate BBAP activity is determined. Determining the ability of the test compound to modulate BBAP activity can be accomplished by monitoring, for example, the survival of a cell which expresses BBAP or the activity of a BBAP-regulated transcription factor. The cell, for example, can be of mammalian origin, e.g., a peripheral blood cell.

The ability of the test compound to modulate BBAP binding to a substrate or to bind to BBAP can also be determined. Determining the ability of the test compound to modulate BBAP binding to a substrate can be accomplished, for example, by coupling the BBAP substrate with a radioisotope or enzymatic label such that binding of the BBAP substrate to BBAP can be determined by detecting the labeled BBAP substrate in a complex. Determining the ability of the test compound to bind BBAP can be accomplished, for example, by coupling the compound with a radioisotope or enzymatic label such that binding of the compound to BBAP can be determined by detecting the labeled BBAP compound in a complex. For example, compounds (e.g., BBAP substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a BBAP substrate) to interact with BBAP without the labeling of any of the interactants. For example, a microphysiometer can be used to detect the interaction of a compound with BBAP without the labeling of either the compound or the BBAP. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and BBAP.

In another embodiment, an assay is a cell-based assay comprising contacting a cell expressing a BBAP target molecule (e.g., a BBAP substrate such as BAL) with a test compound and determining the ability of the test compound to modulate (e.g. stimulate or inhibit) the activity of the BBAP target molecule. Determining the ability of the test compound to modulate the activity of a BBAP target molecule can be accomplished, for example, by determining the ability of the BBAP protein to bind to or interact with the BBAP target molecule, e.g., BAL or DNA.

Determining the ability of the BBAP protein or a biologically active fragment thereof, to bind to or interact with a BBAP target molecule can be accomplished by one of the methods described above for determining direct binding. In a preferred embodiment, determining the ability of the BBAP protein to bind to or interact with a BBAP target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a BBAP protein or biologically active portion thereof is contacted with a test compound and the ability of the test compound to bind to the BBAP protein or biologically active portion thereof is determined. Preferred biologically active portions of the BBAP proteins to be used in assays of the present invention include fragments which participate in interactions with non-BBAP molecules, e.g., fragments with high surface probability scores. Binding of the test compound to the BBAP protein can be determined either directly or indirectly as described above. In a preferred embodiment, the assay includes contacting the BBAP protein or biologically active portion thereof with a known compound which binds BBAP to form an assay mixture, contacting the assay mixture with a test compound, and determining the ability of the test compound to interact with a BBAP protein, wherein determining the ability of the test compound to interact with a BBAP protein comprises determining the ability of the test compound to preferentially bind to BBAP or biologically active portion thereof as compared to the known compound.

In another embodiment, the assay is a cell-free assay in which a BBAP protein or biologically active portion thereof is contacted with a test compound and the ability of the test compound to modulate (e.g., stimulate or inhibit) the activity of the BBAP protein or biologically active portion thereof is determined. Determining the ability of the test compound to modulate the activity of a BBAP protein can be accomplished, for example, by determining the ability of the BBAP protein to bind to a BBAP target molecule by one of the methods described above for determining direct binding. Determining the ability of the BBAP protein to bind to a BBAP target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a BBAP protein can be accomplished by determining the ability of the BBAP protein to further modulate the activity of a downstream effector of a BBAP target molecule. For example, the activity of the effector molecule on an appropriate target can be determined or the binding of the effector to an appropriate target can be determined as previously described.

The cell-free assays of the present invention are amenable to use of both soluble and/or membrane-bound forms of isolated proteins (e.g., BBAP proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either BBAP or its target molecule to facilitate separation of complexed from uncomplexed forms of one or both of the proteins, as well as to accommodate automation of the assay. Binding of a test compound to a BBAP protein, or interaction of a BBAP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/BBAP fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or BBAP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of BBAP binding or activity determined using standard techniques.

Other techniques for immobilizing proteins on matrices can also be used in the screening assays of the invention. For example, either a BBAP protein or a BBAP target molecule can be immobilized utilizing conjugation of biotin and streptavidin. Biotinylated BBAP protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with BBAP protein or target molecules but which do not interfere with binding of the BBAP protein to its target molecule can be derivatized to the wells of the plate, and unbound target or BBAP protein trapped in the wells by antibody conjugation. Methods for detecting such complexes, in addition to those described above for the GST-immobilized complexes, include immunodetection of complexes using antibodies reactive with the BBAP protein or target molecule, as well as enzyme-linked assays which rely on detecting an enzymatic activity associated with the BBAP protein or target molecule.

In another embodiment, modulators of BBAP expression are produced or identified in a method wherein a cell is contacted with a candidate compound and the expression of BBAP mRNA or protein in the cell is determined. The level of expression of BBAP mRNA or protein in the presence of the candidate compound is compared to the level of expression of BBAP mRNA or protein in the absence of the candidate compound. The candidate compound can then be produced or identified as a modulator of BBAP expression based on this comparison. For example, when expression of BBAP mRNA or protein is greater (statistically significantly greater) in the presence of the candidate compound than in its absence, the candidate compound is identified as a stimulator of BBAP mRNA or protein expression (i.e. a stimulator of BBAP mRNA or protein expression is produced). Alternatively, when expression of BBAP mRNA or protein is less (statistically significantly less) in the presence of the candidate compound than in its absence, the candidate compound is produced or identified as an inhibitor of BBAP mRNA or protein expression (i.e. an inhibitor of BBAP mRNA or protein expression is produced). The level of BBAP mRNA or protein expression in the cells can be determined by methods described herein for detecting BBAP mRNA or protein.

In yet another aspect of the invention, the BBAP proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with BBAP ("BBAP-binding proteins" or "BBAP-bp") and are involved in BBAP activity. Such BBAP-binding proteins are also likely to be involved in the propagation of signals by the BBAP proteins or BBAP targets as, for example, downstream elements of a BBAP-mediated signaling pathway. Alternatively, such BBAP-binding proteins are likely to be BBAP inhibitors.

The two-hybrid system is based on the modular nature of most transcription factors, which consist of separable DNA-binding and activation domains. Briefly, the assay utilizes two different DNA constructs. In one construct, the gene that codes for a BBAP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BBAP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the BBAP protein.

This invention further pertains to novel agents identified by the above-described screening assays. Accordingly, it is within the scope of this invention to further use an agent identified and/or produced as described herein in an appropriate animal model. For example, an agent identified and/or produced as described herein (e.g., a BBAP modulating agent, an antisense BBAP nucleic acid molecule, a BBAP-specific antibody, or a BBAP-binding partner) can be used in an animal model to determine the efficacy, toxicity, or side effects of treatment with such an agent. Alternatively, an agent identified and/or produced as described herein can be used in an animal model to determine the mechanism of action of such an agent. Furthermore, this invention pertains to uses of novel agents identified and/or produced by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the BBAP nucleotide sequences, described herein, can be used to map the location of the BBAP genes on a chromosome (further described in Example 1, below). The mapping of the BBAP sequences to chromosomes is an important first step in correlating these sequences with genes associated with disease.

Briefly, BBAP genes can be mapped to chromosomes by preparing PCR primers (preferably 15-25 bp in length) from the BBAP nucleotide sequences. Computer analysis of the BBAP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the BBAP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the BBAP nucleotide sequences to design oligonucleotide primers, sublocalization can be achieved with panels of fragments from specific chromosomes. Other mapping strategies which can similarly be used to map a BBAP sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the BBAP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The BBAP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the BBAP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The BBAP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500-2,000.

If a panel of reagents from BBAP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial BBAP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions of SEQ ID NO:1 are particularly appropriate for this use as greater numbers of polymorphisms occur in the noncoding regions, making it easier to differentiate individuals using this technique. Examples of polynucleotide reagents include the BBAP nucleotide sequences or portions thereof, e.g., fragments derived from the non-coding regions of SEQ ID NO:1 having a length of at least 20 bases, preferably at least 30 bases.

The BBAP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such BBAP probes can be used to identify tissue by species and/or by organ type.

In a similar fashion, these reagents, e.g., BBAP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining BBAP protein and/or nucleic acid expression as well as BBAP activity, in the context of a biological sample (e.g., blood, serum, cells, tissue) to thereby determine whether an individual is afflicted with a disease or disorder, or is at risk of developing a disorder, associated with aberrant BBAP expression or activity, e.g., a malignancy such as a lymphoma, e.g., non-Hodgkin's lymphoma. The invention also provides for prognostic (or predictive) assays for determining whether an individual is at risk of developing a disorder associated with BBAP protein, nucleic acid expression or activity. For example, mutations in a BBAP gene can be assayed in a biological sample. Such assays can be used for prognostic or predictive purpose to thereby phophylactically treat an individual prior to the onset of a disorder characterized by or associated with BBAP protein, nucleic acid expression or activity e.g., a malignancy such as a lymphoma, e.g., non-Hodgkin's lymphoma.

Another aspect of the invention pertains to monitoring the influence of agents (e.g., drugs, compounds) on the expression or activity of BBAP in clinical trials.

These and other agents are described in further detail in the following sections.

1. Diagnostic Assays

An exemplary method for detecting the presence or absence of BBAP protein or nucleic acid in a biological sample involves obtaining a biological sample from a test subject and contacting the biological sample with a compound or an agent capable of detecting BBAP protein or nucleic acid (e.g., mRNA or genomic DNA) that encodes BBAP protein such that the presence of BBAP protein or nucleic acid is detected in the biological sample. A preferred agent for detecting BBAP mRNA or genomic DNA is a labeled nucleic acid probe capable of hybridizing to BBAP mRNA or genomic DNA. The nucleic acid probe can be, for example, a full-length BBAP nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to BBAP mRNA or genomic DNA. Other suitable probes for use in the diagnostic assays of the invention are described herein.

A preferred agent for detecting BBAP protein is an antibody capable of binding to BBAP protein, preferably an antibody with a detectable label. Antibodies can be polyclonal or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect BBAP mRNA, protein, or genomic DNA in a biological sample in vitro as well as in vivo. For example, in vitro techniques for detection of BBAP mRNA include Northern hybridizations and in situ hybridizations. In vitro techniques for detection of BBAP protein include enzyme linked immunosorbent assays (ELISAs), Western blots, immunoprecipitations and immunofluorescence. In vitro techniques for detection of BBAP genomic DNA include Southern hybridizations. Furthermore, in vivo techniques for detection of BBAP protein include introducing into a subject a labeled anti-BBAP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting BBAP protein, mRNA, or genomic DNA, such that the presence of BBAP protein, mRNA or genomic DNA is detected in the biological sample, and comparing the presence of BBAP protein, mRNA or genomic DNA in the control sample with the presence of BBAP protein, mRNA or genomic DNA in the test sample.

The invention also encompasses kits for detecting the presence of BBAP in a biological sample. For example, the kit can comprise a labeled compound or agent capable of detecting BBAP protein or mRNA in a biological sample; means for determining the amount of BBAP in the sample; and means for comparing the amount of BBAP in the sample with a standard. The compound or agent can be packaged in a suitable container. The kit can further comprise instructions for using the kit to detect BBAP protein or nucleic acid.

2. Prognostic Assays

The diagnostic methods described herein can furthermore be utilized to identify subjects having or at risk of developing a disease or disorder associated with aberrant BBAP expression or activity e.g., a malignancy such as a lymphoma, e.g., non-Hodgkin's lymphoma. As used herein, the term "aberrant" includes a BBAP expression or activity which deviates from the wild type BBAP expression or activity. Aberrant expression or activity includes increased or decreased expression or activity, as well as expression or activity which does not follow the wild type developmental pattern of expression or the subcellular pattern of expression. For example, aberrant BBAP expression or activity is intended to include the cases in which a mutation in the BBAP gene causes the BBAP gene to be under-expressed or over-expressed and situations in which such mutations result in a non-functional BBAP protein or a protein which does not function in a wild-type fashion, e.g., a protein which does not interact with a BBAP ligand or one which interacts with a non-BBAP ligand.

The assays described herein, such as the preceding diagnostic assays or the following assays, can be utilized to identify a subject having or at risk of developing a disorder associated with a misregulation in BBAP protein activity or nucleic acid expression, e.g., a malignancy such as a lymphoma, e.g., non-Hodgkin's lymphoma. Alternatively, the prognostic assays can be utilized to identify a subject having or at risk for developing a disorder associated with a misregulation in BBAP protein activity or nucleic acid expression, such as a e.g., a malignancy such as a lymphoma, e.g., non-Hodgkin's lymphoma. Thus, the present invention provides a method for identifying a disease or disorder associated with aberrant BBAP expression or activity in which a test sample is obtained from a subject and BBAP protein or nucleic acid (e.g., mRNA or genomic DNA) is detected, wherein the presence of BBAP protein or nucleic acid is diagnostic for a subject having or at risk of developing a disease or disorder associated with aberrant BBAP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant BBAP expression or activity. For example, such methods can be used to determine whether a subject can be effectively treated with an agent for a e.g., a malignancy such as a lymphoma, e.g., non-Hodgkin's lymphoma. Thus, the present invention provides methods for determining whether a subject can be effectively treated with an agent for a disorder associated with aberrant BBAP expression or activity in which a test sample is obtained and BBAP protein or nucleic acid expression or activity is detected (e.g., wherein the abundance of BBAP protein or nucleic acid expression or activity is diagnostic for a subject that can be administered the agent to treat a disorder associated with aberrant BBAP expression or activity).

The methods of the invention can also be used to detect genetic alterations in a BBAP gene, thereby determining if a subject with the altered gene is at risk for a disorder characterized by misregulation in BBAP protein activity or nucleic acid expression, such as a e.g., a malignancy such as a lymphoma, e.g., non-Hodgkin's lymphoma. In preferred embodiments, the methods include detecting, in a sample of cells from the subject, the presence or absence of a genetic alteration characterized by at least one of an alteration affecting the integrity of a gene encoding a BBAP-protein, or the misexpression of the BBAP gene. For example, such genetic alterations can be detected by ascertaining the existence of at least one of 1) a deletion of one or more nucleotides from a BBAP gene; 2) an addition of one or more nucleotides to a BBAP gene; 3) a substitution of one or more nucleotides of a BBAP gene, 4) a chromosomal rearrangement of a BBAP gene; 5) an alteration in the level of a messenger RNA transcript of a BBAP gene, 6) aberrant modification of a BBAP gene, such as of the methylation pattern of the genomic DNA, 7) the presence of a non-wild type splicing pattern of a messenger RNA transcript of a BBAP gene, 8) a non-wild type level of a BBAP-protein, 9) allelic loss of a BBAP gene, and 10) inappropriate post-translational modification of a BBAP-protein. As described herein, there are a large number of assays known in the art which can be used for detecting alterations in a BBAP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the BBAP-gene (see Abravaya et al. (1995) *Nucleic Acids Res* 23:675-682). This method can include the steps of collecting a sample of cells from a subject, isolating nucleic acid (e.g., genomic DNA or mRNA) from the cells of the sample, contacting the nucleic acid sample with one or more primers which specifically hybridize to a BBAP gene under conditions such that hybridization and amplification of the BBAP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl.*

Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a BBAP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in BBAP can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in BBAP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the BBAP gene and detect mutations by comparing the sequence of the sample BBAP with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be used when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the BBAP gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type BBAP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BBAP cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a BBAP sequence, e.g., a wild-type BBAP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in BBAP genes. For example, single strand conformation polymorphism (SSCP) may be used to detect differences in electrophoretic mobility between mutant and wild type nucleic acids (orita et al. (1989) Proc Natl. Acad Sci USA: 86:2766, see also Cotton (1993) Mutat. Res. 285:125-144; and Hayashi (1992) Genet. Anal. Tech. Appl. 9:73-79). Single-stranded DNA fragments of sample and control BBAP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method uses heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al.

(1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by the use of pre-packaged diagnostic kits which include at least one probe nucleic acid or antibody reagent described herein, which may be conveniently used, e.g., in clinical settings to diagnose patients exhibiting symptoms or family history of a disease or illness involving a BBAP gene such as non-Hodgkin's lymphoma. Such kits can optionally include instructions for use.

Furthermore, any cell type or tissue in which BBAP is expressed may be used in the prognostic assays described herein.

3. Monitoring of Effects During Clinical Trials

Monitoring the influence of agents (e.g., drugs) on the expression or activity of a BBAP protein can be applied not only in basic drug screening, but also in clinical trials. For example, the effectiveness of an agent determined by a screening assay as described herein to increase BBAP gene expression, protein levels, or upregulate BBAP activity, can be monitored in clinical trials of subjects exhibiting decreased BBAP gene expression, protein levels, or downregulated BBAP activity. Alternatively, the effectiveness of an agent determined by a screening assay to decrease BBAP gene expression, protein levels, or downregulate BBAP activity, can be monitored in clinical trials of subjects exhibiting increased BBAP gene expression, protein levels, or upregulated BBAP activity. In such clinical trials, the expression or activity of a BBAP gene, and preferably, other genes that have been implicated in, for example, a BBAP-associated disorder can be used as a "read out" or markers of the phenotype of a particular cell.

For example, and not by way of limitation, genes, including BBAP, that are modulated in cells by treatment with an agent (e.g., compound, drug or small molecule) which modulates BBAP activity (e.g., identified in a screening assay as described herein) can be identified. Thus, to study the effect of agents on BBAP-associated disorders (e.g., malignancies such as non-Hodgkin's lymphoma), for example, in a clinical trial, cells can be isolated and RNA prepared and analyzed for the levels of expression of BBAP and other genes implicated in the BBAP-associated disorder, respectively. The levels of gene expression (e.g., a gene expression pattern) can be quantified by northern blot analysis or RT-PCR, as described herein, or alternatively by measuring the amount of protein produced, by one of the methods described herein, or by measuring the levels of activity of BBAP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a BBAP protein, mRNA, or genomic DNA in the preadministration sample; (iii) obtaining one or more post-administration samples from the subject; (iv) detecting the level of expression or activity of the BBAP protein, mRNA, or genomic DNA in the post-administration samples; (v) comparing the level of expression or activity of the BBAP protein, mRNA, or genomic DNA in the pre-administration sample with the BBAP protein, mRNA, or genomic DNA in the post administration sample or samples; and (vi) altering the administration of the agent to the subject accordingly. For example, increased administration of the agent may be desirable to increase expression or activity of BBAP to lower levels than detected, i.e., to decrease the effectiveness of the agent. According to such an embodiment, BBAP expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant BBAP expression or activity e.g., a malignancy such as a lymphoma, e.g., non-Hodgkin's lymphoma. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the BBAP molecules of the present invention or BBAP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant BBAP expression or activity, by administering to the subject a BBAP molecule or an agent which modulates BBAP expression or at least one BBAP activity. Subjects at risk for a disease which is caused or contributed to by aberrant BBAP expression or activity can be identified by, for example, any or a combination of diagnostic or prognostic assays as described herein. Administration of a prophylactic agent can occur prior to the manifestation of symptoms characteristic of the BBAP aberrancy, such that a disease or disorder is prevented or, alternatively, delayed in its progression. Depending on the type of BBAP aberrancy, for example, a BBAP molecule, BBAP agonist, or BBAP antagonist can be used to treat the subject. The appropriate agent can be determined based on, for example, the screening assays described herein.

2. Therapeutic Methods

Another aspect of the invention pertains to methods of modulating BBAP expression or activity for therapeutic purposes. Accordingly, in an exemplary embodiment, the modulatory method of the invention involves contacting a cell with a BBAP or agent that modulates one or more of the activities of BBAP protein activity associated with the cell. An agent that modulates BBAP protein activity can be an agent as described herein, such as a nucleic acid or a protein, a naturally-occurring target molecule of a BBAP protein (e.g., a BBAP substrate), a BBAP antibody, a BBAP agonist or antagonist, a peptidomimetic of a BBAP agonist or antagonist, or other small molecule. In one embodiment, the agent stimulates one or more BBAP activities. Examples of such stimulatory agents include active BBAP protein and a nucleic acid molecule encoding BBAP that has been introduced into the cell. In another embodiment, the agent inhibits one or more BBAP activities. Examples of such inhibitory agents include antisense BBAP nucleic acid molecules, anti-BBAP antibodies, and BBAP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a BBAP protein or nucleic acid molecule. In one embodiment, the method involves administering an agent (e.g., an agent identified by a screening assay described herein), or combination of agents that modulate (e.g., upregulate or downregulate) BBAP expression or activity. In another embodiment, the method involves administering a BBAP protein or nucleic acid molecule as therapy to compensate for reduced or aberrant BBAP expression or activity.

Stimulation of BBAP activity is desirable in situations in which BBAP is abnormally downregulated and/or in which increased BBAP activity is likely to have a beneficial effect. For example, stimulation of BBAP activity is desirable in situations in which a BBAP molecule is downregulated and/or in which increased BBAP activity is likely to have a beneficial effect. Likewise, inhibition of BBAP activity is desirable in situations in which BBAP is abnormally upregulated and/or in which decreased BBAP activity is likely to have a beneficial effect.

3. Pharmacogenomics

The BBAP molecules of the present invention, as well as agents, or modulators which have a stimulatory or inhibitory effect on BBAP activity (e.g., BBAP gene expression) as identified by a screening assay described herein can be administered to individuals to treat (prophylactically or therapeutically) BBAP-associated disorders (e.g., e.g., malignancies such as non-Hodgkin's lymphoma). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a BBAP molecule or BBAP modulator as well as tailoring the dosage and/or therapeutic regimen of treatment with a BBAP molecule or BBAP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11) δ 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a BBAP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations.

For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a BBAP molecule or BBAP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a BBAP molecule or BBAP modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Identification and Characterization of Human BBAP cDNA

Figure 3:
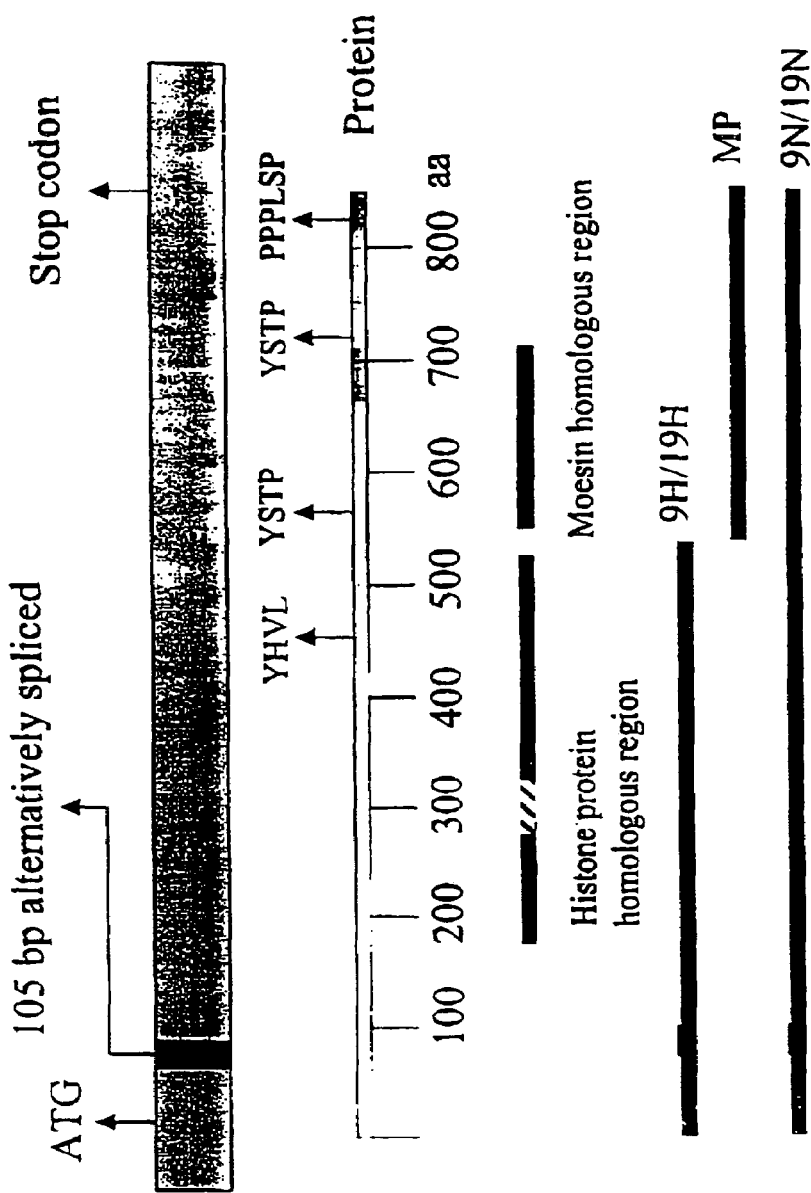
FIG. 3 depicts a schematic diagram of the BAL fragments that were used as baits in the yeast two-hybrid assay.

In this example, the identification and characterization of the gene encoding human BBAP is described. To identify other genes which contribute to the observed differences in clinical outcome in DLB-CLs, yeast two-hybrid screens (Zervos et al. (1993) Cell 72:223-232) were used to identify proteins which bind to or interact with the BAL protein. The BAL fragments that were used as baits in the yeast two-hybrid assay are depicted in FIG. 3. A novel BAL-associated protein termed "B-lymphoma and BAL-associated protein" or "BBAP" has been identified, which specifically interacts with the BAL carboxyl terminal region (the Moesin homologous region of BAL). The nucleotide sequence encoding the human BBAP protein is shown in FIG. 1 and is set forth as SEQ ID NO:1. The full length protein encoded by this nucleic acid comprises about 739 amino acids and has the amino acid sequence shown in FIG. 1 and set forth as SEQ ID NO:2. The coding region (open reading frame) of SEQ ID NO:1 is set forth as SEQ ID NO:3.

The co-association between BBAP and BAL was confirmed by co-transfecting tagged constructs (FLAG-tagged BBAP and HA-tagged BAL) into COS cells, immunoprecipitating BBAP/BAL complexes with a FLAG antibody, blotting the immunoprecipitates, and identify BAL with an HA antibody.

Tissue Distribution of BBAP

Paired northern blot analyses of BBAL and BAL transcripts have demonstrated that these genes are expressed at very similar levels in multiple normal tissues and a variety of hematopoietic cell lines (see FIG. 2).

Mapping of the BBAP Locus

To map the BBAP locus, a BBAP cDNA probe was used to screen a human genomic DNA PAC library (RPCI1). Genomic BBAP-positive PAC clones were used to perform FISH (fluorescence in situ hybridization) on normal human metaphases. In complementary experiments, a somatic cell hybrid panel was analyzed for BBAP sequences. These experiments have demonstrated that BBAP maps to the same clone as BAL at 3q21.

Analysis of the Human BBAP Molecules

The carboxyl terminal region of the BBAP protein is 45% identical to the carboxyl terminus of murine FXI-T1 and 47% identical to the carboxyl terminus of human Deltex. FXI-T1 is the murine homologue of *Drosophila* Deltex, which is differentially expressed in fractionated X-irradiation-induced murine thymomas and contributes to FX-induced leukemogenesis. Human Deltex (the human homologue of *Drosophila* Deltex) is a conserved regulator of Notch signaling and a modulator of basic helix-loop-helix (bHLH) transcription factor activity.

Amino acid analysis of the human BBAP sequence has demonstrated that the human BBAP comprises a C3HC4-type zinc finger motif (at amino acid residues 561-599 of SEQ ID NO:2); three nuclear localization signals (at amino acid residues 20-26, 462-478, and 475-478 of SEQ ID NO:2); and two short coiled-coil domains with 2-heptad repeats (at amino acid residues 347-360 and 391-404 of SEQ ID NO:2).

Human BBAP has an instability index of 50.53, which classifies this protein as unstable.

Taken together, these data indicate that the novel BBAP protein co-associates with BAL in vivo, demonstrates sequence homology with a component of a signal pathway that functions during cell differentiation, and contains a strong nuclear localization signal and a C3HC4-type zinc finger motif. The data further indicate that the BAL/BBAP complex may exert its effect in the nucleus. In addition, the striking similarities in BBAP and BAL transcript abundance in the tissues examined to date indicate that BBAP and BAL may be similarly regulated and that BBAP expression may also be risk-related in DLB-CL.

Tumorigenicity of BBAP Transfectants

BBAP's potential effects on the local growth and distant metastasis of DLB-CL cell lines may further be determined in an in vivo murine model. Constructs containing BBAP are injected subcutaneously or via tail vein into cohorts of SCID mice. Local tumorigenicity and distant metastasis can be scored at periodic intervals as described in Yakushijin Y. et al. (1998)*Blood*, 91:4282-4291.

Development of a BBAP Antibody

In order to generate a BBAP antibody, the BBAP cDNA is cloned into the pGEX expression vector (GST Gene Fusion System, Pharmacia). After sequencing the construct to ensure that the fusion is in frame and that no mutations have been introduced in the BBAP sequence, bacterial cultures containing pGEX-BBAP are treated with IPTG (isopropyl-1-Thio-b-D-Galactopyearanoside) and the GST-Bal fusion protein is induced and affinity-purified on gluthathione-5-agarose beads. Balb-c mice are immunized with the affinity-purified GST-BBAP protein and their spleens harvested for generation of BBAP monoclonal antibodies. Monoclonal antibodies are initially screened for reactivity with pGEX-BBAP and not with pGEX alone using ELISA. Positive hybridoma supernatants are then screened against immunoblotted parental and BBAP DLB-CL transfectants for reactivity with the appropriate-sized BBAP protein.

Role of BBAP in Modulating Cellular Motility and Migration

To investigate the potential role of BBAP in modulating cellular motility and migration, BBAP is cloned into a GFP vector (PEGFP) and an untagged expression vector (pRc-CMV) and pEGFP-BBAP, pRc-CMV BBAP, and vector only transfectants are generated in an aggressive lymphoma cell line that constitutively expresses low levels of BBAP. The effects of BBAP overexpression on the migration of these transfectants is investigated using a transwell system. In initial experiments, BBAP-GFP or GFP-only transfectants are plated in the upper chamber and analyzed for migration to the lower chamber in the presence of the hematopoietic chemoattractant factor, stromal derived factor 1-α (SDF-1α).

Example 2

Expression of Recombinant BBAP Protein in Bacterial Cells

In this example, human BBAP is expressed as a recombinant glutathione-S-transferase (GST) fusion polypeptide in E. coli and the fusion polypeptide is isolated and characterized. Specifically, BBAP is fused to GST and this fusion polypeptide is expressed in E. coli, e.g., strain PEB199. Expression of the GST-BBAP fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant BBAP Protein in COS Cells

To express the BBAP gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire BBAP protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the BBAP DNA sequence is amplified by PCR using two primers. The 5' primer contains the restriction site of interest followed by approximately twenty nucleotides of the BBAP coding sequence starting from the initiation codon; the 3' end sequence contains complementary sequences to the other restriction site of interest, a translation stop codon, the HA tag or FLAG tag and the last 20 nucleotides of the BBAP coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the BBAP gene is inserted in the correct orientation. The ligation mixture is transformed into E. coli cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the BBAP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed, Cold Spring Harbor Laboratory, Cold Spring Harbor, Laboratory Press, Cold Spring Harbor, N.Y., 1989. The expression of the BBAP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the BBAP coding sequence is cloned directly into the polylinker of the pcDNA/Amp vector using the appropriate restriction sites. The resulting plasmid is transfected into COS cells in the manner described above, and the expression of the BBAP polypeptide is detected by radiolabelling and immunoprecipitation using a BBAP specific monoclonal antibody.

Example 4

Subcellular Localization of BBAP and BAL Protein

To gain additional insight into the function of BBAP, a FLAG-tagged BBAP and BAL fused to green fluorescence protein (GFP) were used to determine the subcellular localization of these proteins. COS7 cells were transfected with the FLAG-tagged BBAP and, subsequently, immunofluorescent staining was performed using an anti-Flag and a Rhodamine Red-X-conjugated secondary antibody. Based on the foregoing analysis, it was determined that, contrary to the BAL protein, BBAP localizes primarily to the cytoplasm. Use of an anti-BBAP monoclonal antibody confirmed the cytoplasmic staining, indicating that localization of BBAP to the cytoplasm is not an artifact of fusion to FLAG or overexpression. As indicated in previous studies, BAL localized to the nucleus of COS7 cells transfected with a BAL-GFP construct in the absent of BBAP protein. However, when COS7 cells were co-transfected with BAL-GFP and Flag-tagged BBAP, BAL co-localized with BBAP in the cytoplasm. The foregoing data indicate that BBAP plays an important role in determining the subcellular localization of BAL.

Subcellular fractionation of the DLB-CL cell lines shows that both BBAP and BAL are primarily localized in the cytoplasm, but also exist in the nucleus. The concentration of the two proteins is very similar in both subcellular organelles (nucleus and cytoplasm) in a variety of DLB-CL cell lines (e.g., DHL4, DHL6, DHL7, DHL10), indicating that the endogenous subcellular localization of the BBAP and BAL proteins is similar, unlike the localization of BAL or BBAP when each is present alone in a cell.

Example 5

Co-Association of BBAP and Human DTX1

Studies of human DTX1 (human Deltex) and murine MDTX family members have shown that DTX proteins form homotypic and heterotypic multimers. As indicated above, the BBAP and DTX1 C-termini are highly homologous. To determine whether there is a physical association between BBAP and DTX1, COS7 cells were co-transfected with Flag-tagged BBAP and Myc-tagged DTX1, BBAP was immuno-precipitated with an anti-flag antibody, and the precipitates were analyzed by western blotting. DTX1-Myc was clearly detected in BBAP-Flag immunoprecipitates of cells that were co-transfected with both constructs. The foregoing data confirm that BBAP and DTX1 co-associate in vivo.

Example 6

Suppression of the E47 Promoter

Figure 4:
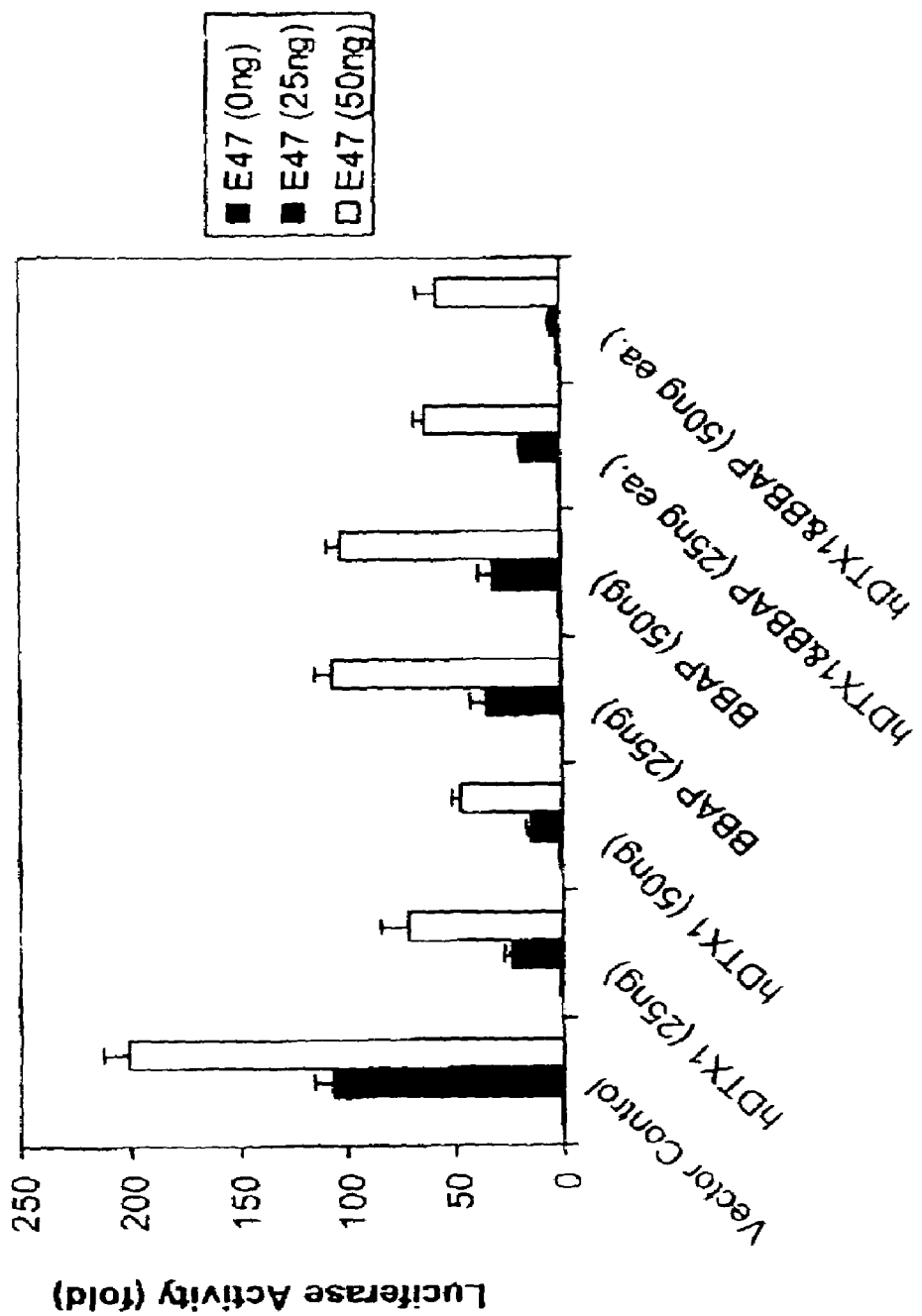
FIG. 4 depicts the results from an expression assay which demonstrates that the BBAP protein has an inhibitory effect on E47 activity. 293 cells were co-transfected with [E5+E2]$_6$ TATA-Luc (50 ng) and null-Renilla luciferase control reporter construct (5 ng), the indicated amounts (0ng, 25 ng, or 50 ng) of the E47mig plasmid encoding E47, and the indicated amounts (0ng, 25 ng, or 50 ng) of the pcDNA-Myc plasmid encoding DTX1 or/and pFLAG-CMV plasmid encoding BBAP. Cell extracts were prepared 44 hours post-transfection. E2+E5 reporter luciferase activity, corrected for null-Renillar luciferase activity, is expressed as fold activation relative to control 293 cells not expressing E47, DTX1 and BBAP. Error bars indicate standard deviation of two independent experiments.

Activation of Notch signaling in cultured mammalian cells results in the suppression of transcriptional activation by a human bHLH protein, E47 (Ordentlich, P. et al. (1998) *Mol. Cell. Biol.* 18, 22302239). For example, the transcription of an E47-responsive reporter gene is specifically suppressed when E47 is co-expressed with an activated form of human Notch1 or DTX1 (Ordentlich, P. et al. supra and Matsuno, K. et al. (1998) *Nat. Genet.* 19, 74-78). In this experiment, the effect of the BBAP protein on E47 activity was evaluated using a Luciferase reporter construct driven by an E47-responsive promoter. As shown in FIG. 4, the relative activity of the E47-responsive reporter was suppressed significantly when E47 was co-expressed with human DTX1, in a dosage sensitive fashion. Under the same conditions, E47 activity was also inhibited when E47 was co-expressed with human BBAP. However, the inhibition of E47 activity by BBAP was weaker than the activity inhibition observed with DTX1, and the suppression of reporter activity was less dosage dependent. The foregoing observations indicate that the BBAP protein has an inhibitory effect on E47 activity that is similar to that seen with human DTX1. Unlike human DTX1, BBAP's effect on E47 may be indirect.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide which is encoded by a nucleic acid molecule comprising the nucleotide sequence of SEQ ID NO:1 or SEQ ID NO:3.

2. The isolated polypeptide of claim 1, comprising the amino acid sequence of SEQ ID NO:2.

3. The polypeptide of claim 1, further comprising heterologous amino acid sequences.

4. A method of producing a polypeptide comprising culturing a host cell transfected with an expression vector comprising a nucleic acid molecule encoding a polypeptide of claim 1 in an appropriate culture medium to, thereby, produce the polypeptide.

5. An isolated polypeptide comprising the amino acid sequence of SEQ ID NO:2.

* * * * *

SEQUENCE LISTING

```
<160> NUMBER OF SEQ ID NOS: 7

<210> SEQ ID NO 1
<211> LENGTH: 2762
<212> TYPE: DNA
<213> ORGANISM: Homo sapiens
<220> FEATURE:
<221> NAME/KEY: CDS
<222> LOCATION: (167)..(2383)

<400> SEQUENCE: 1
ccctcgacct cgagatccat tgtgctctaa aggcggctct gccgggaaca gggagggacc      60
tccagggaag cgaaactgaa actttgcgcc cagtccgcag ggcgggccgc gcctttaccg     120
cccagctgcc tcccggagcc cccgcgccct cccgacgcgc agagcc atg gcc tcc       175
                                                  Met Ala Ser
                                                   1 cac ctg cgc ccg ccg tcc ccg ctc ctc gtg cgg gtg tac aag tcc ggc      223
His Leu Arg Pro Pro Ser Pro Leu Leu Val Arg Val Tyr Lys Ser Gly
      5                  10                  15 ccc cga gta cga agg aag ctg gag agc tac ttc cag agc tct aag tcc      271
Pro Arg Val Arg Arg Lys Leu Glu Ser Tyr Phe Gln Ser Ser Lys Ser
 20                  25                  30                  35 tcg ggc ggc ggg gag tgc acg gtc agc acc cag gaa cac gaa gcc ccg      319
Ser Gly Gly Gly Glu Cys Thr Val Ser Thr Gln Glu His Glu Ala Pro
                  40                  45                  50 ggc acc ttc cgg gtg gag ttc agt gaa agg gca gct aag gag aga gtg      367
Gly Thr Phe Arg Val Glu Phe Ser Glu Arg Ala Ala Lys Glu Arg Val
              55                  60                  65 ttg aaa aaa gga gag cac caa ata ctt gtt gac gaa aaa cct gtg ccc      415
Leu Lys Lys Gly Glu His Gln Ile Leu Val Asp Glu Lys Pro Val Pro
          70                  75                  80 att ttc ctg gta ccc act gaa aat tca ata aag aag aac acg aga cct      463
```

```
                Ile Phe Leu Val Pro Thr Glu Asn Ser Ile Lys Lys Asn Thr Arg Pro
                    85                  90                  95 caa att tct tca ctg aca caa tca caa gca gaa aca ccg tct ggt gat            511
Gln Ile Ser Ser Leu Thr Gln Ser Gln Ala Glu Thr Pro Ser Gly Asp
100                 105                 110                 115 atg cat caa cat gaa gga cat att cct aat gct gtg gat tcc tgt ctc            559
Met His Gln His Glu Gly His Ile Pro Asn Ala Val Asp Ser Cys Leu
                    120                 125                 130 caa aag atc ttt ctt act gta aca gct gac ctg aac tgt aac ctg ttc            607
Gln Lys Ile Phe Leu Thr Val Thr Ala Asp Leu Asn Cys Asn Leu Phe
            135                 140                 145 tcc aaa gag cag agg gca tac ata acc aca ctg tgc cct agt atc aga            655
Ser Lys Glu Gln Arg Ala Tyr Ile Thr Thr Leu Cys Pro Ser Ile Arg
        150                 155                 160 aaa atg gaa ggt cac gat gga att gag aag gtg tgt ggt gac ttc caa            703
Lys Met Glu Gly His Asp Gly Ile Glu Lys Val Cys Gly Asp Phe Gln
165                 170                 175 gac att gaa aga ata cat caa ttt ttg agt gag cag ttc ctg gaa agt            751
Asp Ile Glu Arg Ile His Gln Phe Leu Ser Glu Gln Phe Leu Glu Ser
180                 185                 190                 195 gag cag aaa caa caa ttt tcc cct tca atg aca gag agg aag cca ctc            799
Glu Gln Lys Gln Gln Phe Ser Pro Ser Met Thr Glu Arg Lys Pro Leu
                    200                 205                 210 agt cag cag gag agg gac agc tgc att tct cct tct gaa cca gaa acc            847
Ser Gln Gln Glu Arg Asp Ser Cys Ile Ser Pro Ser Glu Pro Glu Thr
            215                 220                 225 aag gca gaa caa aaa agc aac tat ttt gaa gtt ccc ttg cct tac ttt            895
Lys Ala Glu Gln Lys Ser Asn Tyr Phe Glu Val Pro Leu Pro Tyr Phe
        230                 235                 240 gaa tac ttt aaa tat atc tgt cct gat aaa atc aac tca ata gag aaa            943
Glu Tyr Phe Lys Tyr Ile Cys Pro Asp Lys Ile Asn Ser Ile Glu Lys
245                 250                 255 aga ttt ggt gta aac att gaa atc cag gag agt tct cca aat atg gtc            991
Arg Phe Gly Val Asn Ile Glu Ile Gln Glu Ser Ser Pro Asn Met Val
260                 265                 270                 275 tgt tta gat ttc atc tca agt cga tca ggt gac ctg gaa gca gct cgt           1039
Cys Leu Asp Phe Ile Ser Ser Arg Ser Gly Asp Leu Glu Ala Ala Arg
                    280                 285                 290 gag tct ttt gct agt gaa ttt cag aag aac aca gaa cct ctg aag caa           1087
Glu Ser Phe Ala Ser Glu Phe Gln Lys Asn Thr Glu Pro Leu Lys Gln
            295                 300                 305 gaa tgt gtc tct tta gca gac agt aag cag gca aat aaa ttc aaa cag           1135
Glu Cys Val Ser Leu Ala Asp Ser Lys Gln Ala Asn Lys Phe Lys Gln
        310                 315                 320 gaa ttg aat cac cag ttt aca aag ctc ctt ata aag gag aaa gga ggc           1183
Glu Leu Asn His Gln Phe Thr Lys Leu Leu Ile Lys Glu Lys Gly Gly
325                 330                 335 gaa tta act ctc ctt ggg acc caa gat gac att tca gct gcc aaa caa           1231
Glu Leu Thr Leu Leu Gly Thr Gln Asp Asp Ile Ser Ala Ala Lys Gln
340                 345                 350                 355 aaa atc tct gaa gct ttt gtc aag ata cct gtg aaa cta ttt gct gcc           1279
Lys Ile Ser Glu Ala Phe Val Lys Ile Pro Val Lys Leu Phe Ala Ala
                    360                 365                 370 aat tac atg atg aat gta att gag gtt gat agt gcc cac tat aaa ctt           1327
Asn Tyr Met Met Asn Val Ile Glu Val Asp Ser Ala His Tyr Lys Leu
            375                 380                 385 tta gaa act gaa tta cta cag gag ata tca gag atc gaa aaa agg tat           1375
Leu Glu Thr Glu Leu Leu Gln Glu Ile Ser Glu Ile Glu Lys Arg Tyr
        390                 395                 400
```

```
gac att tgc agc aag gtt tct gag aaa ggt cag aaa acc tgc att ctg        1423
Asp Ile Cys Ser Lys Val Ser Glu Lys Gly Gln Lys Thr Cys Ile Leu
405                 410                 415 ttt gaa tcc aag gac agg cag gta gat cta tct gtg cat gct tat gca        1471
Phe Glu Ser Lys Asp Arg Gln Val Asp Leu Ser Val His Ala Tyr Ala
420                 425                 430                 435 agt ttc atc gat gcc ttt caa cat gcc tca tgt cag ttg atg aga gaa        1519
Ser Phe Ile Asp Ala Phe Gln His Ala Ser Cys Gln Leu Met Arg Glu
                440                 445                 450 gtt ctt tta ctg aag tct ttg ggc aag gag aga aag cac tta cat cag        1567
Val Leu Leu Leu Lys Ser Leu Gly Lys Glu Arg Lys His Leu His Gln
455                 460                 465 acc aag ttt gct gat gac ttt aga aaa aga cat cca aat gta cac ttt        1615
Thr Lys Phe Ala Asp Asp Phe Arg Lys Arg His Pro Asn Val His Phe
        470                 475                 480 gtg cta aat caa gag tca atg act ttg act ggt ttg cca aat cac ctt        1663
Val Leu Asn Gln Glu Ser Met Thr Leu Thr Gly Leu Pro Asn His Leu
485                 490                 495 gca aag gcg aag cag tat gtt cta aaa gga gga gga atg tct tca ttg        1711
Ala Lys Ala Lys Gln Tyr Val Leu Lys Gly Gly Gly Met Ser Ser Leu
500                 505                 510                 515 gct gga aag aaa ttg aaa gag ggt cat gaa aca ccg atg gac att gat        1759
Ala Gly Lys Lys Leu Lys Glu Gly His Glu Thr Pro Met Asp Ile Asp
                520                 525                 530 agc gat gat tcc aaa gca gct tct ccg cca ctc aag ggc tct gtg agt        1807
Ser Asp Asp Ser Lys Ala Ala Ser Pro Pro Leu Lys Gly Ser Val Ser
        535                 540                 545 tct gag gcc tca gaa ctg gac aag aag gaa aag ggc atc tgt gtc atc        1855
Ser Glu Ala Ser Glu Leu Asp Lys Lys Glu Lys Gly Ile Cys Val Ile
550                 555                 560 tgt atg gac acc att agt aac aaa aaa gtg cta cca aag tgc aag cat        1903
Cys Met Asp Thr Ile Ser Asn Lys Lys Val Leu Pro Lys Cys Lys His
565                 570                 575 gaa ttc tgc gcc cct tgt atc aac aaa gcc atg tca tat aag cca atc        1951
Glu Phe Cys Ala Pro Cys Ile Asn Lys Ala Met Ser Tyr Lys Pro Ile
580                 585                 590                 595 tgt ccc aca tgc cag act tcc tat ggt att cag aaa gga aat cag cca        1999
Cys Pro Thr Cys Gln Thr Ser Tyr Gly Ile Gln Lys Gly Asn Gln Pro
                600                 605                 610 gag gga agc atg gtt ttc act gtt tca aga gac tca ctt cca ggt tat        2047
Glu Gly Ser Met Val Phe Thr Val Ser Arg Asp Ser Leu Pro Gly Tyr
        615                 620                 625 gag tcc ttt ggc acc att gtg att act tat tct atg aaa gca ggc ata        2095
Glu Ser Phe Gly Thr Ile Val Ile Thr Tyr Ser Met Lys Ala Gly Ile
630                 635                 640 caa aca gaa gaa cac cca aac cca gga aag aga tac cct gga ata cag        2143
Gln Thr Glu Glu His Pro Asn Pro Gly Lys Arg Tyr Pro Gly Ile Gln
645                 650                 655 cga act gca tac ttg cct gat aat aag gaa gga agg aag gtt ttg aaa        2191
Arg Thr Ala Tyr Leu Pro Asp Asn Lys Glu Gly Arg Lys Val Leu Lys
660                 665                 670                 675 ctg ctt tat agg gcc ttt gac caa aag ctg att ttt aca gtg ggg tac        2239
Leu Leu Tyr Arg Ala Phe Asp Gln Lys Leu Ile Phe Thr Val Gly Tyr
                680                 685                 690 tct cgc gta tta gga gtc tca gat gtc atc act tgg aat gat att cac        2287
Ser Arg Val Leu Gly Val Ser Asp Val Ile Thr Trp Asn Asp Ile His
        695                 700                 705 cac aaa aca tcc cgg ttt gga gga cca gaa atg tat ggc tat cct gat        2335
His Lys Thr Ser Arg Phe Gly Gly Pro Glu Met Tyr Gly Tyr Pro Asp
710                 715                 720
```

```
cct tct tac ctg aaa cgt gtc aaa gag gag ctg aaa gcc aaa gga att    2383
Pro Ser Tyr Leu Lys Arg Val Lys Glu Glu Leu Lys Ala Lys Gly Ile
        725                 730                 735 gagtaagaca actgctggaa gatgtcttaa atcaagcttt caaaaaaata tattttagga  2443
ggctgattta atgccagtct aaatcctat gtagaaagga ctttgaaatt tttcttctca   2503
agaaatggtt tgtataagaa taacaatctg ctagtctgtc atttctggag tgatactttt  2563
ttttttgaga cggagtctgc tctgtcgctc gcactggagt gcagtggcat gatctcggct  2623
cactgcaagc tccgcctccc aggttcatgc cattctccta cctcagcctc ccgagtagct  2683
gggactacag gcgcccactt tagagcacaa tggatctcga ggaacattct ctcttcaaaa  2743
agaaaaaagg tgaagacct                                               2762

<210> SEQ ID NO 2
<211> LENGTH: 739
<212> TYPE: PRT
<213> ORGANISM: Homo sapiens

<400> SEQUENCE: 2

Met Ala Ser His Leu Arg Pro Pro Ser Pro Leu Leu Val Arg Val Tyr
 1               5                  10                  15

Lys Ser Gly Pro Arg Val Arg Lys Leu Glu Ser Tyr Phe Gln Ser
            20                  25                  30

Ser Lys Ser Ser Gly Gly Gly Glu Cys Thr Val Ser Thr Gln Glu His
        35                  40                  45

Glu Ala Pro Gly Thr Phe Arg Val Glu Phe Ser Glu Arg Ala Ala Lys
    50                  55                  60

Glu Arg Val Leu Lys Lys Gly Glu His Gln Ile Leu Val Asp Glu Lys
 65                  70                  75                  80

Pro Val Pro Ile Phe Leu Val Pro Thr Glu Asn Ser Ile Lys Lys Asn
                85                  90                  95

Thr Arg Pro Gln Ile Ser Ser Leu Thr Gln Ser Gln Ala Glu Thr Pro
            100                 105                 110

Ser Gly Asp Met His Gln His Glu Gly His Ile Pro Asn Ala Val Asp
        115                 120                 125

Ser Cys Leu Gln Lys Ile Phe Leu Thr Val Thr Ala Asp Leu Asn Cys
    130                 135                 140

Asn Leu Phe Ser Lys Glu Gln Arg Ala Tyr Ile Thr Thr Leu Cys Pro
145                 150                 155                 160

Ser Ile Arg Lys Met Glu Gly His Asp Gly Ile Glu Lys Val Cys Gly
                165                 170                 175

Asp Phe Gln Asp Ile Glu Arg Ile His Gln Phe Leu Ser Glu Gln Phe
            180                 185                 190

Leu Glu Ser Glu Gln Lys Gln Gln Phe Ser Pro Ser Met Thr Glu Arg
        195                 200                 205

Lys Pro Leu Ser Gln Gln Glu Arg Asp Ser Cys Ile Ser Pro Ser Glu
    210                 215                 220

Pro Glu Thr Lys Ala Glu Gln Lys Ser Asn Tyr Phe Glu Val Pro Leu
225                 230                 235                 240

Pro Tyr Phe Glu Tyr Phe Lys Tyr Ile Cys Pro Asp Lys Ile Asn Ser
                245                 250                 255

Ile Glu Lys Arg Phe Gly Val Asn Ile Glu Ile Gln Glu Ser Ser Pro
            260                 265                 270

Asn Met Val Cys Leu Asp Phe Ile Ser Ser Arg Ser Gly Asp Leu Glu
```

-continued

|  | 275 |  |  | 280 |  |  | 285 |  |  |  |  |
| --- | --- | --- | --- | --- | --- | --- | --- | --- | --- | --- | --- |
| Ala | Ala | Arg | Glu | Ser | Phe | Ala | Ser | Glu | Phe | Gln | Lys | Asn | Thr | Glu | Pro |
| 290 | | | | | 295 | | | | 300 | | | | | | |
| Leu | Lys | Gln | Glu | Cys | Val | Ser | Leu | Ala | Asp | Ser | Lys | Gln | Ala | Asn | Lys |
| 305 | | | | 310 | | | | | 315 | | | | | | 320 |
| Phe | Lys | Gln | Glu | Leu | Asn | His | Gln | Phe | Thr | Lys | Leu | Leu | Ile | Lys | Glu |
| | | | | 325 | | | | | 330 | | | | | 335 | |
| Lys | Gly | Gly | Glu | Leu | Thr | Leu | Leu | Gly | Thr | Gln | Asp | Asp | Ile | Ser | Ala |
| | | | 340 | | | | | 345 | | | | | 350 | | |
| Ala | Lys | Gln | Lys | Ile | Ser | Glu | Ala | Phe | Val | Lys | Ile | Pro | Val | Lys | Leu |
| | | | 355 | | | | | 360 | | | | | 365 | | |
| Phe | Ala | Ala | Asn | Tyr | Met | Met | Asn | Val | Ile | Glu | Val | Asp | Ser | Ala | His |
| | 370 | | | | | 375 | | | | | 380 | | | | |
| Tyr | Lys | Leu | Leu | Glu | Thr | Glu | Leu | Leu | Gln | Glu | Ile | Ser | Glu | Ile | Glu |
| 385 | | | | | 390 | | | | | 395 | | | | | 400 |
| Lys | Arg | Tyr | Asp | Ile | Cys | Ser | Lys | Val | Ser | Glu | Lys | Gly | Gln | Lys | Thr |
| | | | | 405 | | | | | 410 | | | | | 415 | |
| Cys | Ile | Leu | Phe | Glu | Ser | Lys | Asp | Arg | Gln | Val | Asp | Leu | Ser | Val | His |
| | | | | 420 | | | | | 425 | | | | | 430 | |
| Ala | Tyr | Ala | Ser | Phe | Ile | Asp | Ala | Phe | Gln | His | Ala | Ser | Cys | Gln | Leu |
| | | | 435 | | | | | 440 | | | | | 445 | | |
| Met | Arg | Glu | Val | Leu | Leu | Leu | Lys | Ser | Leu | Gly | Lys | Glu | Arg | Lys | His |
| | 450 | | | | | 455 | | | | | 460 | | | | |
| Leu | His | Gln | Thr | Lys | Phe | Ala | Asp | Asp | Phe | Arg | Lys | Arg | His | Pro | Asn |
| 465 | | | | | 470 | | | | | 475 | | | | | 480 |
| Val | His | Phe | Val | Leu | Asn | Gln | Glu | Ser | Met | Thr | Leu | Thr | Gly | Leu | Pro |
| | | | | 485 | | | | | 490 | | | | | 495 | |
| Asn | His | Leu | Ala | Lys | Ala | Lys | Gln | Tyr | Val | Leu | Lys | Gly | Gly | Gly | Met |
| | | | 500 | | | | | 505 | | | | | 510 | | |
| Ser | Ser | Leu | Ala | Gly | Lys | Lys | Leu | Lys | Glu | Gly | His | Glu | Thr | Pro | Met |
| | | 515 | | | | | 520 | | | | | 525 | | | |
| Asp | Ile | Asp | Ser | Asp | Ser | Lys | Ala | Ala | Ser | Pro | Pro | Leu | Lys | Gly |
| | 530 | | | | | 535 | | | | | 540 | | | | |
| Ser | Val | Ser | Ser | Glu | Ala | Ser | Glu | Leu | Asp | Lys | Lys | Glu | Lys | Gly | Ile |
| 545 | | | | | 550 | | | | | 555 | | | | | 560 |
| Cys | Val | Ile | Cys | Met | Asp | Thr | Ile | Ser | Asn | Lys | Lys | Val | Leu | Pro | Lys |
| | | | | 565 | | | | | 570 | | | | | 575 | |
| Cys | Lys | His | Glu | Phe | Cys | Ala | Pro | Cys | Ile | Asn | Lys | Ala | Met | Ser | Tyr |
| | | | 580 | | | | | 585 | | | | | 590 | | |
| Lys | Pro | Ile | Cys | Pro | Thr | Cys | Gln | Thr | Ser | Tyr | Gly | Ile | Gln | Lys | Gly |
| | | | 595 | | | | | 600 | | | | | 605 | | |
| Asn | Gln | Pro | Glu | Gly | Ser | Met | Val | Phe | Thr | Val | Ser | Arg | Asp | Ser | Leu |
| | 610 | | | | | 615 | | | | | 620 | | | | |
| Pro | Gly | Tyr | Glu | Ser | Phe | Gly | Thr | Ile | Val | Ile | Thr | Tyr | Ser | Met | Lys |
| 625 | | | | | 630 | | | | | 635 | | | | | 640 |
| Ala | Gly | Ile | Gln | Thr | Glu | Glu | His | Pro | Asn | Pro | Gly | Lys | Arg | Tyr | Pro |
| | | | | 645 | | | | | 650 | | | | | 655 | |
| Gly | Ile | Gln | Arg | Thr | Ala | Tyr | Leu | Pro | Asp | Asn | Lys | Glu | Gly | Arg | Lys |
| | | | 660 | | | | | 665 | | | | | 670 | | |
| Val | Leu | Lys | Leu | Leu | Tyr | Arg | Ala | Phe | Asp | Gln | Lys | Leu | Ile | Phe | Thr |
| | | 675 | | | | | 680 | | | | | 685 | | | |
| Val | Gly | Tyr | Ser | Arg | Val | Leu | Gly | Val | Ser | Asp | Val | Ile | Thr | Trp | Asn |
| | 690 | | | | | 695 | | | | | 700 | | | | |

```
Asp Ile His His Lys Thr Ser Arg Phe Gly Gly Pro Glu Met Tyr Gly
705                 710                 715                 720

Tyr Pro Asp Pro Ser Tyr Leu Lys Arg Val Lys Glu Glu Leu Lys Ala
            725                 730                 735

Lys Gly Ile

<210> SEQ ID NO 3
<211> LENGTH: 2217
<212> TYPE: DNA
<213> ORGANISM: Homo sapiens
<220> FEATURE:
<221> NAME/KEY: CDS
<222> LOCATION: (1)..(2217)

<400> SEQUENCE: 3
```

| | | | | | | | | | | | | | | | | |
|---|---|---|---|---|---|---|---|---|---|---|---|---|---|---|---|---|
| atg | gcc | tcc | cac | ctg | cgc | ccg | ccg | tcc | ccg | ctc | ctc | gtg | cgg | gtg | tac | 48 |
| Met | Ala | Ser | His | Leu | Arg | Pro | Pro | Ser | Pro | Leu | Leu | Val | Arg | Val | Tyr | |
| 1 | | | | 5 | | | | | 10 | | | | | 15 | | |
| aag | tcc | ggc | ccc | cga | gta | cga | agg | aag | ctg | gag | agc | tac | ttc | cag | agc | 96 |
| Lys | Ser | Gly | Pro | Arg | Val | Arg | Arg | Lys | Leu | Glu | Ser | Tyr | Phe | Gln | Ser | |
| | | | 20 | | | | | 25 | | | | | 30 | | | |
| tct | aag | tcc | tcg | ggc | ggc | ggg | gag | tgc | acg | gtc | agc | acc | cag | gaa | cac | 144 |
| Ser | Lys | Ser | Ser | Gly | Gly | Gly | Glu | Cys | Thr | Val | Ser | Thr | Gln | Glu | His | |
| | 35 | | | | | 40 | | | | | 45 | | | | | |
| gaa | gcc | ccg | ggc | acc | ttc | cgg | gtg | gag | ttc | agt | gaa | agg | gca | gct | aag | 192 |
| Glu | Ala | Pro | Gly | Thr | Phe | Arg | Val | Glu | Phe | Ser | Glu | Arg | Ala | Ala | Lys | |
| 50 | | | | | 55 | | | | | 60 | | | | | | |
| gag | aga | gtg | ttg | aaa | aaa | gga | gag | cac | caa | ata | ctt | gtt | gac | gaa | aaa | 240 |
| Glu | Arg | Val | Leu | Lys | Lys | Gly | Glu | His | Gln | Ile | Leu | Val | Asp | Glu | Lys | |
| 65 | | | | | 70 | | | | | 75 | | | | | 80 | |
| cct | gtg | ccc | att | ttc | ctg | gta | ccc | act | gaa | aat | tca | ata | aag | aag | aac | 288 |
| Pro | Val | Pro | Ile | Phe | Leu | Val | Pro | Thr | Glu | Asn | Ser | Ile | Lys | Lys | Asn | |
| | | | | 85 | | | | | 90 | | | | | 95 | | |
| acg | aga | cct | caa | att | tct | tca | ctg | aca | caa | tca | caa | gca | gaa | aca | ccg | 336 |
| Thr | Arg | Pro | Gln | Ile | Ser | Ser | Leu | Thr | Gln | Ser | Gln | Ala | Glu | Thr | Pro | |
| | | | | 100 | | | | | 105 | | | | | 110 | | |
| tct | ggt | gat | atg | cat | caa | cat | gaa | gga | cat | att | cct | aat | gct | gtg | gat | 384 |
| Ser | Gly | Asp | Met | His | Gln | His | Glu | Gly | His | Ile | Pro | Asn | Ala | Val | Asp | |
| | | | 115 | | | | | 120 | | | | | 125 | | | |
| tcc | tgt | ctc | caa | aag | atc | ttt | ctt | act | gta | aca | gct | gac | ctg | aac | tgt | 432 |
| Ser | Cys | Leu | Gln | Lys | Ile | Phe | Leu | Thr | Val | Thr | Ala | Asp | Leu | Asn | Cys | |
| | 130 | | | | | 135 | | | | | 140 | | | | | |
| aac | ctg | ttc | tcc | aaa | gag | cag | agg | gca | tac | ata | acc | aca | ctg | tgc | cct | 480 |
| Asn | Leu | Phe | Ser | Lys | Glu | Gln | Arg | Ala | Tyr | Ile | Thr | Thr | Leu | Cys | Pro | |
| 145 | | | | | 150 | | | | | 155 | | | | | 160 | |
| agt | atc | aga | aaa | atg | gaa | ggt | cac | gat | gga | att | gag | aag | gtg | tgt | ggt | 528 |
| Ser | Ile | Arg | Lys | Met | Glu | Gly | His | Asp | Gly | Ile | Glu | Lys | Val | Cys | Gly | |
| | | | | 165 | | | | | 170 | | | | | 175 | | |
| gac | ttc | caa | gac | att | gaa | aga | ata | cat | caa | ttt | ttg | agt | gag | cag | ttc | 576 |
| Asp | Phe | Gln | Asp | Ile | Glu | Arg | Ile | His | Gln | Phe | Leu | Ser | Glu | Gln | Phe | |
| | | | 180 | | | | | 185 | | | | | 190 | | | |
| ctg | gaa | agt | gag | cag | aaa | caa | caa | ttt | tcc | cct | tca | atg | aca | gag | agg | 624 |
| Leu | Glu | Ser | Glu | Gln | Lys | Gln | Gln | Phe | Ser | Pro | Ser | Met | Thr | Glu | Arg | |
| | | | 195 | | | | | 200 | | | | | 205 | | | |
| aag | cca | ctc | agt | cag | cag | gag | agg | gac | agc | tgc | att | tct | cct | tct | gaa | 672 |
| Lys | Pro | Leu | Ser | Gln | Gln | Glu | Arg | Asp | Ser | Cys | Ile | Ser | Pro | Ser | Glu | |
| | 210 | | | | | 215 | | | | | 220 | | | | | |
| cca | gaa | acc | aag | gca | gaa | caa | aaa | agc | aac | tat | ttt | gaa | gtt | ccc | ttg | 720 |
| Pro | Glu | Thr | Lys | Ala | Glu | Gln | Lys | Ser | Asn | Tyr | Phe | Glu | Val | Pro | Leu | |
| 225 | | | | | 230 | | | | | 235 | | | | | 240 | |

-continued

```
cct tac ttt gaa tac ttt aaa tat atc tgt cct gat aaa atc aac tca        768
Pro Tyr Phe Glu Tyr Phe Lys Tyr Ile Cys Pro Asp Lys Ile Asn Ser
            245                 250                 255 ata gag aaa aga ttt ggt gta aac att gaa atc cag gag agt tct cca        816
Ile Glu Lys Arg Phe Gly Val Asn Ile Glu Ile Gln Glu Ser Ser Pro
        260                 265                 270 aat atg gtc tgt tta gat ttc atc tca agt cga tca ggt gac ctg gaa        864
Asn Met Val Cys Leu Asp Phe Ile Ser Ser Arg Ser Gly Asp Leu Glu
    275                 280                 285 gca gct cgt gag tct ttt gct agt gaa ttt cag aag aac aca gaa cct        912
Ala Ala Arg Glu Ser Phe Ala Ser Glu Phe Gln Lys Asn Thr Glu Pro
290                 295                 300 ctg aag caa gaa tgt gtc tct tta gca gac agt aag cag gca aat aaa        960
Leu Lys Gln Glu Cys Val Ser Leu Ala Asp Ser Lys Gln Ala Asn Lys
305                 310                 315                 320 ttc aaa cag gaa ttg aat cac cag ttt aca aag ctc ctt ata aag gag       1008
Phe Lys Gln Glu Leu Asn His Gln Phe Thr Lys Leu Leu Ile Lys Glu
                325                 330                 335 aaa gga ggc gaa tta act ctc ctt ggg acc caa gat gac att tca gct       1056
Lys Gly Gly Glu Leu Thr Leu Leu Gly Thr Gln Asp Asp Ile Ser Ala
            340                 345                 350 gcc aaa caa aaa atc tct gaa gct ttt gtc aag ata cct gtg aaa cta       1104
Ala Lys Gln Lys Ile Ser Glu Ala Phe Val Lys Ile Pro Val Lys Leu
        355                 360                 365 ttt gct gcc aat tac atg atg aat gta att gag gtt gat agt gcc cac       1152
Phe Ala Ala Asn Tyr Met Met Asn Val Ile Glu Val Asp Ser Ala His
    370                 375                 380 tat aaa ctt tta gaa act gaa tta cta cag gag ata tca gag atc gaa       1200
Tyr Lys Leu Leu Glu Thr Glu Leu Leu Gln Glu Ile Ser Glu Ile Glu
385                 390                 395                 400 aaa agg tat gac att tgc agc aag gtt tct gag aaa ggt cag aaa acc       1248
Lys Arg Tyr Asp Ile Cys Ser Lys Val Ser Glu Lys Gly Gln Lys Thr
                405                 410                 415 tgc att ctg ttt gaa tcc aag gac agg cag gta gat cta tct gtg cat       1296
Cys Ile Leu Phe Glu Ser Lys Asp Arg Gln Val Asp Leu Ser Val His
            420                 425                 430 gct tat gca agt ttc atc gat gcc ttt caa cat gcc tca tgt cag ttg       1344
Ala Tyr Ala Ser Phe Ile Asp Ala Phe Gln His Ala Ser Cys Gln Leu
        435                 440                 445 atg aga gaa gtt ctt tta ctg aag tct ttg ggc aag gag aga aag cac       1392
Met Arg Glu Val Leu Leu Leu Lys Ser Leu Gly Lys Glu Arg Lys His
    450                 455                 460 tta cat cag acc aag ttt gct gat gac ttt aga aaa aga cat cca aat       1440
Leu His Gln Thr Lys Phe Ala Asp Asp Phe Arg Lys Arg His Pro Asn
465                 470                 475                 480 gta cac ttt gtg cta aat caa gag tca atg act ttg act ggt ttg cca       1488
Val His Phe Val Leu Asn Gln Glu Ser Met Thr Leu Thr Gly Leu Pro
                485                 490                 495 aat cac ctt gca aag gcg aag cag tat gtt cta aaa gga gga gga atg       1536
Asn His Leu Ala Lys Ala Lys Gln Tyr Val Leu Lys Gly Gly Gly Met
            500                 505                 510 tct tca ttg gct gga aag aaa ttg aaa gag ggt cat gaa aca ccg atg       1584
Ser Ser Leu Ala Gly Lys Lys Leu Lys Glu Gly His Glu Thr Pro Met
        515                 520                 525 gac att gat agc gat gat tcc aaa gca gct tct ccg cca ctc aag ggc       1632
Asp Ile Asp Ser Asp Asp Ser Lys Ala Ala Ser Pro Pro Leu Lys Gly
    530                 535                 540 tct gtg agt tct gag gcc tca gaa ctg gac aag aag gaa aag ggc atc       1680
Ser Val Ser Ser Glu Ala Ser Glu Leu Asp Lys Lys Glu Lys Gly Ile
```

```
                 545                 550                 555                 560
tgt gtc atc tgt atg gac acc att agt aac aaa aaa gtg cta cca aag        1728
Cys Val Ile Cys Met Asp Thr Ile Ser Asn Lys Lys Val Leu Pro Lys
                565                 570                 575 tgc aag cat gaa ttc tgc gcc cct tgt atc aac aaa gcc atg tca tat        1776
Cys Lys His Glu Phe Cys Ala Pro Cys Ile Asn Lys Ala Met Ser Tyr
            580                 585                 590 aag cca atc tgt ccc aca tgc cag act tcc tat ggt att cag aaa gga        1824
Lys Pro Ile Cys Pro Thr Cys Gln Thr Ser Tyr Gly Ile Gln Lys Gly
        595                 600                 605 aat cag cca gag gga agc atg gtt ttc act gtt tca aga gac tca ctt        1872
Asn Gln Pro Glu Gly Ser Met Val Phe Thr Val Ser Arg Asp Ser Leu
    610                 615                 620 cca ggt tat gag tcc ttt ggc acc att gtg att act tat tct atg aaa        1920
Pro Gly Tyr Glu Ser Phe Gly Thr Ile Val Ile Thr Tyr Ser Met Lys
625                 630                 635                 640 gca ggc ata caa aca gaa gaa cac cca aac cca gga aag aga tac cct        1968
Ala Gly Ile Gln Thr Glu Glu His Pro Asn Pro Gly Lys Arg Tyr Pro
                645                 650                 655 gga ata cag cga act gca tac ttg cct gat aat aag gaa gga agg aag        2016
Gly Ile Gln Arg Thr Ala Tyr Leu Pro Asp Asn Lys Glu Gly Arg Lys
            660                 665                 670 gtt ttg aaa ctg ctt tat agg gcc ttt gac caa aag ctg att ttt aca        2064
Val Leu Lys Leu Leu Tyr Arg Ala Phe Asp Gln Lys Leu Ile Phe Thr
        675                 680                 685 gtg ggg tac tct cgc gta tta gga gtc tca gat gtc atc act tgg aat        2112
Val Gly Tyr Ser Arg Val Leu Gly Val Ser Asp Val Ile Thr Trp Asn
    690                 695                 700 gat att cac cac aaa aca tcc cgg ttt gga gga cca gaa atg tat ggc        2160
Asp Ile His His Lys Thr Ser Arg Phe Gly Gly Pro Glu Met Tyr Gly
705                 710                 715                 720 tat cct gat cct tct tac ctg aaa cgt gtc aaa gag gag ctg aaa gcc        2208
Tyr Pro Asp Pro Ser Tyr Leu Lys Arg Val Lys Glu Glu Leu Lys Ala
                725                 730                 735 aaa gga att                                                            2217
Lys Gly Ile <210> SEQ ID NO 4
<211> LENGTH: 66
<212> TYPE: PRT
<213> ORGANISM: Artificial Sequence
<220> FEATURE:
<223> OTHER INFORMATION: Xaa's at positions 2,36,38,41,42, and 65 may be
      any amino acid
<223> OTHER INFORMATION: Xaa at position 3 may be Ile or Val
<223> OTHER INFORMATION: Any 19 of the Xaa's between positions 5 and
      34 may be absent; intended to equal a range of 11-30
      amino acids, where Xaa can be any amino acid
<223> OTHER INFORMATION: Xaa at position 39 may be Phe, Ile, or Leu
<223> OTHER INFORMATION: Xaa at position 44 may be Ile, Leu, or Met
<223> OTHER INFORMATION: Any 8 of the Xaa's between positions 45 and
      62 may be absent; intended to equal a range of 10-18
      amino acids, where Xaa may be any amino acid
<223> OTHER INFORMATION: Description of Artificial Sequence: motif

<400> SEQUENCE: 4

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Cys Xaa His Xaa Xaa Cys Xaa Xaa Cys Xaa Xaa Xaa Xaa Xaa
        35                  40                  45
```

-continued

```
Xaa Xaa Xaa Xaa Xaa Xaa Xaa Xaa Xaa Xaa Xaa Xaa Xaa Xaa Cys Pro
    50                  55                  60
Xaa Cys
 65

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: motif

<400> SEQUENCE: 5

Arg Lys Arg His
  1

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: motif

<400> SEQUENCE: 6

Pro Arg Val Arg Arg Lys Leu
  1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: motif

<400> SEQUENCE: 7

Arg Lys His Leu His Gln Thr Lys Phe Ala Asp Asp Phe Arg Lys Arg
  1               5                  10                  15
His
```